US010561379B2

(12) United States Patent
Choi

(10) Patent No.: US 10,561,379 B2
(45) Date of Patent: Feb. 18, 2020

(54) IN VIVO POSITRON EMISSION TOMOGRAPHY-BASED PERFUSION/BLOOD POOL IMAGING USING LABELED ERYTHROCYTES

(71) Applicant: H. LEE MOFFITT CANCER CENTER AND RESEARCH INSTITUTE, INC., Tampa, FL (US)

(72) Inventor: Jung Wook Choi, Wesley Chapel, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 0 days.

(21) Appl. No.: 15/780,568

(22) PCT Filed: Jan. 11, 2017

(86) PCT No.: PCT/US2017/013063
§ 371 (c)(1),
(2) Date: May 31, 2018

(87) PCT Pub. No.: WO2017/123666
PCT Pub. Date: Jul. 20, 2017

(65) Prior Publication Data
US 2018/0344264 A1 Dec. 6, 2018

Related U.S. Application Data

(60) Provisional application No. 62/277,205, filed on Jan. 11, 2016.

(51) Int. Cl.
*A61B 6/03* (2006.01)
*A61K 35/18* (2015.01)
(Continued)

(52) U.S. Cl.
CPC .............. *A61B 6/037* (2013.01); *A61K 35/18* (2013.01); *A61K 51/0491* (2013.01); *A61K 51/1203* (2013.01); *A61B 6/481* (2013.01)

(58) Field of Classification Search
None
See application file for complete search history.

(56) References Cited

U.S. PATENT DOCUMENTS 8,329,141 B2 12/2012 Wong
8,540,968 B2 9/2013 Weichert et al.
(Continued)

FOREIGN PATENT DOCUMENTS

EP 3249409 11/2017

OTHER PUBLICATIONS

Bailey, D. L. et al. "[68]Ga PET Ventilation and Perfusion Lung Imaging-Current Status and Future Challenges" *Seminars in Nuclear Medicine*, Sep. 2016, pp. 428-435, vol. 46, No. 5.
(Continued)

*Primary Examiner* — Yara B Green
(74) *Attorney, Agent, or Firm* — Saliwanchik, Lloyd & Eisenschenk

(57) ABSTRACT

The present invention concerns a positron emission tomography (PET) contrast agent or imaging tracer comprising a red blood cell (RBC) internally labeled with 2-deoxy-2-($^{18}$F) fluoro-D-glucose (FDG); a method of preparing RBCs of a human or non-human animal for PET, comprising labeling RBCs in vitro with FDG to produce FDG-labeled RBCs; a method for in vivo imaging of RBCs using PET, comprising: introducing RBCs internally labeled with FDG (FDG-RBCs) into the circulatory system of a human or non-human animal subject in vivo; and PET imaging the introduced FDG-RBCs in the subject; a composition useful for labeling RBCs, and a kit for labeling RBCs.

20 Claims, 14 Drawing Sheets

(51) Int. Cl.
  *A61K 51/12* (2006.01)
  *A61K 51/04* (2006.01)
  *A61B 6/00* (2006.01)

(56) References Cited

U.S. PATENT DOCUMENTS

| | | | |
|---|---|---|---|
| 2001/0046470 | A1 | 11/2001 | Morita |
| 2007/0217998 | A1* | 9/2007 | Wong ............... A61K 51/02 424/1.65 |
| 2008/0311036 | A1* | 12/2008 | Wang ............... A61K 51/04 424/1.69 |
| 2012/0039796 | A1* | 2/2012 | Markou ............... A61K 9/107 424/1.11 |
| 2013/0144051 | A1* | 6/2013 | Mueller ............... B01J 19/004 536/122 |
| 2014/0119621 | A1 | 5/2014 | Uber, III |
| 2014/0163368 | A1* | 6/2014 | Rousso ............... A61B 6/037 600/436 |
| 2014/0241604 | A1 | 8/2014 | Wang et al. |
| 2016/0287734 | A1* | 10/2016 | Rashidian ............... A61K 51/08 |
| 2016/0299150 | A1* | 10/2016 | Chorev ............... G01N 33/566 |

OTHER PUBLICATIONS

Basuli, F. et al. "Synthesis of fluorine-18 radio-labeled serum albumins for PET blood pool imaging" *Nuclear Medicine and Biology*, Mar. 2015, pp. 219-225, vol. 42, No. 3.
Bonte, F. J. et al. "TC-99m HMPAO Brain Blood Flow Imaging in the Dementias with Histopathologic Correlation in 73 Patients" *International Journal of Molecular Imaging*, 2011, 409101, 3rd.
Burow, R. D. et al. "Analysis of left ventricular function from multiple gated acquisition cardiac blood pool imaging. Comparison to contrast angiography" *Circulation*, Dec. 1977, pp. 1024-1028, vol. 56, No. 6.
Cox, B. et al. "The Sweet Spot: FDG and other 2-carbon glucose analogs for multi-modal metabolic imaging of tumor metabolism" *American Journal of Nuclear Medicine and Molecular Imaging*, 2015, pp. 1-13, vol. 5, No. 1.
De Langen, A. J. et al. "Use of $H_2^{15}$O-PET and DCE-MRI to measure tumor blood flow" *The Oncologist*, Jun. 2008, pp. 631-644, vol. 13, No. 6.
Fahey, F. H. "Data Acquisition in PET Imaging" *J. Nucl Med Technol*, 2002, pp. 39-49, vol. 30.
Fan, A. P. et al. "Comparison of cerebral blood flow measurement with [$^{15}$O]-water positron emission tomography and arterial spin labeling magnetic resonance imaging: A systematic review" *Journal of Cerebral Blood Flow and Metabolism*, May 2016, pp. 842-861, vol. 36, No. 5.
Flower, M. A. et al. "$^{62}$Cu-PTSM and PET used for the assessment of angiotensin II-induced blood flow changes in patients with colorectal liver metastases" *European Journal of Nuclear Medicine*, Jan. 2001, pp. 99-103, vol. 28, No. 1.
Goffin, K. et al. "Neuronuclear assessment of patients with epilepsy" *Seminars in Nuclear Medicine*, Jul. 2008, pp. 227-239, vol. 38, No. 4.
Green, M. A. et al. "Copper(II) Bis(thiosemicarbazone) Complexes as Potential Tracers for Evaluation of Cerebral and Myocardial Blood flow with PET" *Journal of Nuclear Medicine*, pp. 1549-1557, Sep. 1988, vol. 29, No. 9.
Green, M. A. et al. "Copper-62-labeled Pyruvaldehyde Bis($N^4$-methylthiosemicarbazonato)copper(II): Synthesis and Evaluation as a Positron Emission Tomography Tracer for Cerebral and Myocardial Perfusion" *Journal of Nuclear Medicine*, Dec. 1990, pp. 1989-1996, vol. 31, No. 12.
Hajjawi, O. "Glucose transport in human red blood cells" *American Journal of Biomedical and Life Sciences*, 2013, pp. 44-52, vol. 1., No. 3.

Haynes, N. G. et al. "Performance of a $^{62}$Zn/$^{62}$Cu generator in clinical trials of PET perfusion agent $^{62}$Cu-PTSM" *Journal of Nuclear Medicine*, Feb. 2000, pp. 309-314, vol. 41, No. 2.
Herrero, P. et al. "Regional Myocardial Perfusion Assessed with Generator-Produced Copper-62-PTSM and PET" *Journal of Nuclear Medicine*, Aug. 1996, pp. 1294-1300, vol. 37, No. 8.
Ibaraki, M. et al. "Quantification of cerebral blood flow and oxygen metabolism with 3-dimensional PET and $^{15}$O: validation by comparison with 2-dimensional PET" *Journal of Nuclear Medicine*, Jan. 2008, pp. 50-59, vol. 49, No. 1.
Lin, L. "A Concordance Correlation of Coefficient to Evaluate Reproducibility" *Biometrics*, 1989, pp. 255-268, vol. 45, No. 1.
Lodge, M. A. et al. "Reproducibility of tumor blood flow quantification with $^{15}$O-water PET" *Journal of Nuclear Medicine*, Oct. 2008, pp. 1620-1627, vol. 49, No. 10.
MacDonald, A. et al. "Infrequently performed studies in nuclear medicine: Part 1" *Journal of nuclear medicine technology*, Sep. 2008, pp. 132-143, vol. 36, No. 3.
Montel-Hagen, A. et al. "The Glut1 and Glut4 glucose transporters are differentially expressed during perinatal and postnatal erythropoiesis" *Blood*, Dec. 1, 2008, pp. 4729-4738, vol. 112, No. 12.
Montel-Hagen, A. et al. "Erythrocyte Glut1 triggers DHA uptake in mammals unable to synthesize Vitamin C" *Cell*, Mar. 21, 2008, pp. 1039-1048, 132.
Niu, G. et al. "In Vivo Labeling of Serum Albumin for PET" *Journal of Nuclear Medicine*, Jul. 2014, pp. 1150-1156, vol. 55, No. 7.
Patlak, C. S. et al. "Graphical evaluation of blood-to-brain transfer constants from multiple-time uptake data" *Journal of Cerebral Blood Flow and Metabolism*, Mar. 1983, pp. 1-7, vol. 3, No. 1.
Rahmin, A. et al. "PET versus SPECT: strengths, limitations and challenges" *Nuclear Medicine Communications*, 2008, pp. 193-207, vol. 29, No. 3.
Saatchi, K. et al. "Long-circulating non-toxic blood pool imaging agent based on hyperbranched polyglycerols" *International Journal of Pharmaceutics*, Jan. 17, 2012, pp. 418-427, vol. 422, Nos. 1-2.
Shelton, M. E. et al. "Assessment of regional myocardial and renal blood flow with copper-PTSM and positron emission tomography" *Circulation*, Sep. 1990, pp. 990-997, vol. 82, No. 3.
Tahara, N. et al. "2-deoxy-2-[$^{18}$F]Fluoro-D-Mannose Positron Emission Tomography Imaging in Atherosclerosis" *Nature Medicine*, 2014, pp. 215-221, vol. 20, No. 2.
Thorne, D. A. et al. "Bleeding rates Necessary for Detecting Acute Gastrointestinal Bleeding with Technetium-99m-Labeled Red Blood Cells in an Experimental Model" *Journal of Nuclear Medicine*, Apr. 1987, pp. 514-520, vol. 28, No. 4.
Viskupicova, J. et al. "Effect of high glucose concentrations on human erythrocytes in vitro" *Redox Biology*, Aug. 2015, pp. 381-387, vol. 5.
Wallhaus, T. R. et al. "Copper-62-pyruvaldehyde bis(N-methyl-thiosemicarbazone) PET imaging in the detection of coronary artery disease in humans" *Journal of Nuclear Cardiology*, Jan.-Feb. 2001, pp. 67-74, vol. 8, No. 1.
Wang, Z. G. et al. "Technological value of SPECT/CT fusion imaging for the diagnosis of lower gastrointestinal bleeding" *Genetics and Molecular Research*, Nov. 24, 2015, pp. 14947-14955, vol. 14, No. 4.
Welch, M. J. et al. "The potential role of generator-produced radiopharmaceuticals in clinical PET" *Journal of Nuclear Medicine*, Feb. 2000, pp. 315-317, vol. 41, No. 2.
Wong, T. Z. et al. "PET of hypoxia and perfusion with $^{62}$Cu-ATSM and $^{62}$Cu-PTSM using a $^{62}$Zn/$^{62}$Cu generator" *American Journal of Roentgenology*, Feb. 2008, pp. 427-432, vol. 190, No. 2.
Zhang, T. et al. "PET with $^{62}$Cu-ATSM and $^{62}$Cu-PTSM is a useful imaging tool for hypoxia and perfusion in pulmonary lesions" *American Journal of Roentgenology*, Nov. 2013, pp. W698-W706, vol. 201, No. 5.

\* cited by examiner

IN VIVO POSITRON EMISSION TOMOGRAPHY-BASED PERFUSION/BLOOD POOL IMAGING USING LABELED ERYTHROCYTES

CROSS-REFERENCE TO RELATED APPLICATIONS

The present application is the National Stage of International Application No. PCT/US2017/013063, filed Jan. 11, 2017, which claims the benefit of U.S. Provisional Application Ser. No. 62/277,205, filed Jan. 11, 2016, which is hereby incorporated by reference herein in its entirety, including any figures, tables, nucleic acid sequences, amino acid sequences, or drawings.

BACKGROUND OF THE INVENTION

Positron emission tomography (PET) is a nuclear medicine imaging modality based on the measurement of positron emission from radio-labelled tracer molecules. These positron-emitting radionuclides (radiotracers) allow biologic processes to be measured and partial or whole body images to be obtained which demonstrate sites of radiotracer accumulation. The system detects pairs of gamma rays emitted indirectly by the tracer molecule, which is introduced into the body on a biologically active molecule. Two-dimensional or three-dimensional images of tracer concentration within the body are then constructed by computer analysis.

Fludeoxyglucose (18F), or fludeoxyglucose F 18, also commonly called fluorodeoxyglucose and abbreviated [$^{18}$F] FDG, 18F-FDG or FDG, is a radiopharmaceutical used in PET. Chemically, it is 2-deoxy-2-($^{18}$F)fluoro-D-glucose, a glucose analog, with the positron-emitting radioactive isotope fluorine-18 substituted for the normal hydroxyl group at the 2' position in the glucose molecule.

If the biologically active molecule selected for PET is FDG, the concentrations of tracer imaged will indicate tissue metabolic activity as it corresponds to the regional glucose uptake. PET is both a medical and research tool. It is used heavily in clinical oncology (medical imaging of tumors and the search for metastases), and for clinical diagnosis of certain diffuse brain diseases such as those causing various types of dementias. PET is also an important research tool to map human brain and heart function, and support drug development. PET is also used in pre-clinical studies using animals, where it allows repeated investigations in the same subjects. This is particularly valuable in cancer research, as it results in an increase in the statistical power of the data (subjects can act as their own control) and substantially reduces the numbers of animals required for a given study.

Other imaging modalities include x-ray computed tomography (CT), magnetic resonance imaging (MM) and functional magnetic resonance imaging (fMRI), ultrasound, and single-photon emission computed tomography (SPECT).

BRIEF SUMMARY OF THE INVENTION

The subject invention concerns a novel contrast agent useful for in vivo positron emission tomography (PET)-based nuclear imaging.

Blood comprising erythrocytes, also known as red blood cells (RBCs), can be collected from the human or animal subject, and externally (ex vivo) incubated with 2-deoxy-2-($^{18}$F)fluoro-D-glucose (FDG) to produce RBCs that are internally labelled with FDG (FDG-RBCs). Optionally, before the labelling step, the RBCs are purified (separated from) one or more (optionally, all) of the other components of the collected blood, such as white blood cells. In some embodiments, the RBCs are labelled within about 24 hours after they are collected. Optionally, the RBCs may be stored prior to labelling. Optionally, after the labelling step, FDG-RBCs are purified from unincorporated (free) FDG, such as by centrifugation and washing. The FDG-RBCs are then re-introduced intravascularly into same subject, or introduced into a different subject, and the radiotracer activity within the subject's circulation is imaged in vivo using a PET scanner.

In vivo clinical PET imaging of FDG-RBCs can potentially be used for blood perfusion-specific clinical imaging tests, including dynamic cardiac contractility assessment and localization of sites of occult gastrointestinal (GI) bleeding. In particular, it is expected to yield equivalent to superior imaging results in comparison to the Technetium-99m labeled red blood cell nuclear scan, with significantly reduced radiation exposure to the subject.

Thus, the invention includes a PET contrast agent comprising a human or animal RBC internally labeled with FDG; a method of preparing RBCs of a human or non-human animal for PET, comprising labeling RBCs in vitro with FDG to produce FDG-labeled RBCs; and a method for obtaining a PET image or PET-CT image of FDG-RBCs within a subject, the method comprising introducing the FDG-RBCs into a subject, and subjecting the FDG-labeled RBCs to a PET procedure in vivo in which a PET image PET-CT image is obtained. In each embodiment of each aspect of the invention described herein supra and infra, the $^{18}$F radionuclide may be substituted for another positron-emitting radionuclide such as $^{124}$I or $^{76}$Br, $^{64}$Cu, or $^{68}$Ga. In each embodiment of each aspect of the invention described herein supra and infra, FDG may be substituted for another glucose analog. In some embodiments, the glucose analog comprises 18F. In some embodiments, the glucose analog comprises another positron emitting radionuclide. In some embodiments, the glucose analog is one that is taken up by RBCs via one or more GLUT transporters.

In some embodiments, the methods of the invention are useful as a diagnostic process to efficiently incorporate radiolabeled fludeoxyglucose ($^{18}$F-FDG) into red blood cells (RBCs/erythrocytes) ex vivo, allowing the measurement of, for example, left ventricle function and occult bowel bleeding via positron emission tomography (PET) after reinjection into the same patient or a different patient.

In some embodiments, labeling is carried out by, optionally washing RBCs with buffer (e.g., EDTA buffer), adding $^{18}$F-FDG, incubating at a temperature in the range of about 25 degrees to about 37 degrees Celsius, or higher, for a sufficient period of time for uptake, centrifuging the cells, removing supernatant, optionally washing the cells with buffer (e.g., EDTA buffer), and centrifuging the cells.

In some embodiments, labeling is carried out by washing 250 μL day-old human red blood cells with EDTA buffer, adding 1-2 mCi $^{18}$F-FDG (Cardinal Health), incubating at 37° C. for 30 minutes, centrifuging cells for 10 minutes at 1000×g, removing supernatant, washing cells with EDTA buffer, and centrifuging the cells.

$^{18}$F-FDG PET offers significantly less radiation exposure than alternative technology for radiolabeling RBCs with Tc-99m, as well as increased resolution, particularly after 3-D scanning, than the alternative diagnostic technologies, echocardiogram (for ventricular function) or capsule endoscopy (for bowel bleeding).

BRIEF DESCRIPTION OF THE DRAWINGS

FIG. 8: Whole body PET image of a control splenectomized NSG mouse injected with 79 µCuries of free 18F-FDG. Note normal marked FDG uptake in the myocardium (arrow), and physiologic FDG excretion into the kidneys and bladder (arrowheads). FIG. 9: Whole body PET image of a splenectomized NSG mouse injected with 69 µCuries of 18F-FDG-labeled human erythrocytes. Note intraluminal tracer activity within the cardiac chambers (filled arrowheads), and in the major vessels of the neck (white arrows) and of the abdomen-pelvis (filled arrows).

FIG. 10: Axial (left), coronal (middle), and sagittal (right) fused PET-CT images of the mouse heart show intense physiologic FDG uptake by myocardium of the left ventricle in a splenectomized NSG mouse injected with 2.2 MBq of free 18F-FDG. Circles at the crosshairs indicate lumen of the left ventricle. FIG. 11: Axial (left), coronal (middle), and sagittal (right) fused PET-CT images of the mouse heart show FDG activity within the lumen of the cardiac chambers (circles at the crosshairs) in a splenectomized NSG mouse injected with 1.7 MBq of 18F-FDG-labeled human erythrocytes. Pulmonary perfusion about the heart is also visualized.

FIG. 12: FDG TAC of heart of control mouse injected with free FDG shows a steady increase in FDG activity over time, consistent with gradual FDG uptake by myocardium. FIG. 13: TAC of heart of mouse injected with FDG-labeled RBCs shows expected blood pool activity of FDG-labeled human erythrocytes with immediately high FDG activity (≤1 minute) followed by a small initial decline (4-14 minutes) presumably related to renal excretion of residual free and/or small amount of released intracellular RBC-FDG, and then a plateau (14-30 minutes). The plateau suggests absence of progressive RBC hemolysis/FDG renal excretion in vivo.

FIG. 15A: Whole body PET image of a control splenectomized NSG mouse injected with 1.7 MBq of free 18F-FDG. FIG. 15B: Whole body ECG-gated PET image of a splenectomized NSG mouse injected with 10.4 MBq of 18F-FDG-labeled human erythrocytes. N=4 in FDG-RBC injected mouse group.

FIG. 16A: FDG time activity curve (TAC) of the heart of a control mouse injected with free FDG shows a steady increase in FDG activity over time, consistent with gradual FDG uptake by myocardium. FIG. 16B: TAC of the heart of a mouse injected with FDG-labeled RBCs shows expected blood pool activity of FDG-labeled human erythrocytes with immediately high FDG activity (≤1 minute) followed by a small initial decline (4-14 minutes) and then activity plateau (14-30 minutes).

DETAILED DESCRIPTION OF THE INVENTION

Figure 1A:
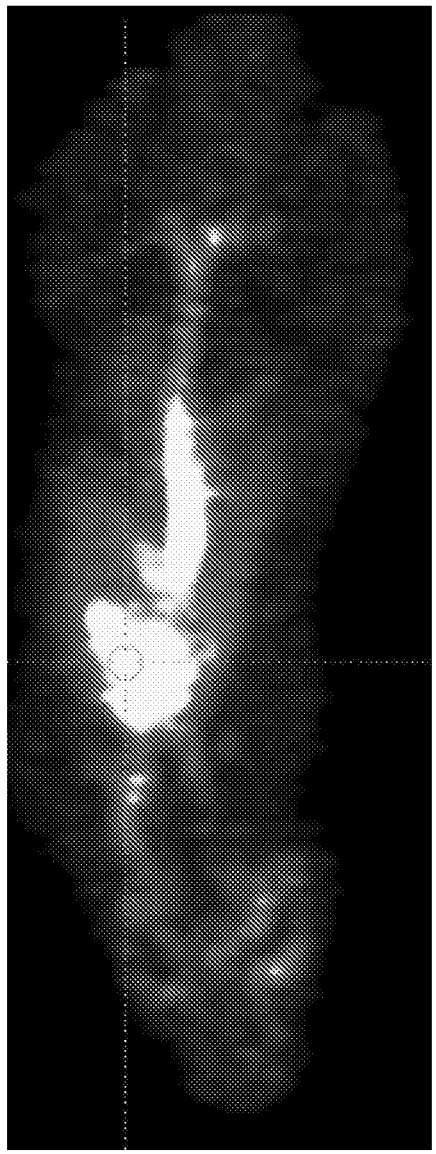
FIG. 1A shows the PET image of a splenectomized NSG immunodeficient mouse following injection of approximately 47 microCuries of FDG-labeled human erythrocytes via tail vein catheter. The top of the image shows the mouse tail and the bottom of the image shows the mouse head. The green circular region of interest marker lies over the heart. Curvilinear areas of increased tracer activity correspond to mouse vessels, with the most activity localized to the abdominal aorta and inferior vena cava. Weaker homogeneous activity about the heart and extending around the upper abdominal vessels corresponds to pulmonary vascular bed. Note relative absence of tracer excretion in the kidneys or significant bladder uptake.

This invention concerns the novel application of in vivo positron emission tomography (PET)-based nuclear imaging of erythrocytes labeled with the PET radio-isotope tracer 2-deoxy-2-($^{18}$F)fluoro-D-glucose (FDG). Erythrocytes (red blood cells (RBCs)) can be collected from a subject and externally (ex vivo) incubated with FDG. Optionally, after blood is collected, and prior to incubation with FDG, the RBCs are purified (separated from) one or more (optionally, all) of the other components of the collected blood, such as white blood cells (e.g., by differential centrifugation or flow cytometry). The FDG-labelled RBCs are optionally purified from unincorporated (free) FDG by centrifugation and cell washing.

The RBCs are then intravascularly (intravenously or intra-arterially) re-introduced into the subject, or introduced into a different subject, and the radiotracer activity within the subject's circulation is imaged using a PET scanner. In vivo clinical PET imaging of FDG-labeled RBCs can potentially be used for blood perfusion-specific clinical imaging tests, including dynamic cardiac contractility assessment and localization of sites of occult internal bleeding. In particular, it is expected to yield equivalent to superior imaging results in comparison to the Technetium-99m-labeled RBC nuclear scan, with significantly reduced radiation exposure to the subject.

The FDG-RBCs have clinical applications for imaging blood perfusion-dependent phenomena, such as tumor perfusion or tissue ischemia. The FDG-RBCs, compositions, kits, and methods of the invention may be used for detection or monitoring the progress of any condition (e.g., disease or disorder) involving altered (abnormal) blood perfusion.

In vitro data has been collected, demonstrating that the amount of intracellular FDG incorporation into human erythrocytes is sufficient for detection and imaging of perfusion-dependent processes in a clinical PET scanner.

In addition to in vivo imaging, the human or animal FDG-RBCs are useful for imaging in vitro, such as an in vitro model of in vivo circulatory systems, by PET imaging the FDG-RBCs in vitro (e.g., in the in vitro model).

In some embodiments, a PET scanner is used to carry out the in vivo or in vitro imaging. In some embodiments, the PET scanner is a PET-CT scanner. PET scans are increasingly read alongside CT or magnetic resonance imaging (MRI) scans, with the combination (called "co-registration") giving both anatomic and metabolic information (i.e., what the structure is, and what it is doing biochemically). Because PET imaging can be more useful in combination with anatomical imaging, such as CT, modern PET scanners are now available with integrated multi-detector-row CT scanners (PET-CT). Because the two scans can be performed in immediate sequence during the same session, with the subject not changing position between the two types of scans, the two sets of images are more-precisely registered, so that areas of abnormality on the PET imaging can be more accurately correlated with anatomy on the CT images.

This invention includes a new method for non-invasively imaging blood within a subject using the PET. This is achieved by internally incorporating the radioactive tracer compound FDG into red blood cells. This technique may be used to image blood perfusion-based biological processes in the subject's body, such as imaging heart motion as well detecting sites of internal bleeding in the body. Potential advantages of the invention include a significant reduction in radiation dose exposure to the patient with equivalent to superior imaging results.

In some embodiments, the RBCs that are labeled with FDG were obtained from the subject to which FDG-RBCs are to be introduced (i.e., the RBCs are autologous to the subject). In other embodiments, the RBCs are allogeneic to the subject. In other embodiments, the RBCs are xenogeneic to the subject. The RBCs may be genetically modified or non-genetically modified cells.

The invention concerns a PET contrast agent comprising a human or non-human animal RBC internally labeled with 2-deoxy-2-($^{18}$F)fluoro-D-glucose (FDG), and a method of preparing RBCs of a human or non-human animal for positron emission tomography (PET), comprising labeling RBCs in vitro with FDG to produce FDG-labeled RBCs. The invention also includes in vitro or an in vivo imaging methods using the FDG-RBCs of the invention. In each embodiment of each aspect of the invention described herein supra and infra, the $^{18}$F radionuclide may be substituted for another positron-emitting radionuclide such as $^{124}$I or $^{76}$Br, $^{64}$Cu, or $^{68}$Ga. In each embodiment of each aspect of the invention described herein supra and infra, FDG may be substituted for another glucose analog. In some embodiments, the glucose analog is a deoxyglucose analog. Examples of glucose analogs that may be utilized include but are not limited to 2-deoxy-2-18F fluoro-D-mannose (also known as FDM; see Tahara N. et al., 2014), and those set forth in Figure 1 of Cox. B. et al., 2008, which is incorporated herein by reference in its entirety. In some embodiments, the glucose analog comprises 18F as the radionuclide. In some embodiments, the glucose analog comprises a positron emitting radionuclide other than 18F. In some embodiments, the glucose analog is one that is taken up by RBCs via one or more GLUT transporters (e.g., GLUT1). In one embodiment, the glucose analog is one that utilizes a different mechanism for uptake into the RBCs, such as 1,3,4,6-tetra-ace-tyl-2-[$^{18}$F]-2-deoxy-D-glucose ($^{18}$F-AFDG).

One aspect of the invention includes a method for in vivo imaging of RBCs using PET, comprising: introducing RBCs internally labeled with FDG (FDG-RBCs) into the circulatory system of a human or non-human animal subject in vivo; and PET imaging the introduced FDG-RBCs in the subject. The phrase "in vivo imaging" as used herein refers to methods of detecting the presence of a detectable moiety (e.g., an optically detectable moiety) in a whole, live human or non-human animal subject. In vivo imaging may be used to provide two-dimensional as well as three-dimensional (3D) images of a subject or parts of a subject, providing anatomic localization of the FDG-RBCs.

Suitable equipment is used to carry out the imaging according to the imaging modality. For example, for in vivo PET imaging, a PET detector typically comprises an array of thousands of scintillation crystals and hundreds of photomultiplier tubes (PMTs) in detection blocks arranged in a circular pattern (a detector ring) around the subject. The scintillation crystals convert the gamma radiation into light which is detected and amplified by the PMTs.

The effective amount of FDG-RBCs to be introduced will vary with the imaging procedure and can be determined by one of ordinary skill in the art. In some embodiments, the volume of fluid containing FDG-RBCs introduced into a subject is in the range of 5 to 40 milliliters (e.g., 20 milliliters) and may vary with a particular subject and condition.

In some embodiments of the in vivo imaging method, the introducing step comprises introducing the FDG-RBCs intravascularly (e.g., by intravenous or intra-arterial injection or infusion).

In some embodiments, the method comprises, prior to introducing, withdrawing RBCs from the subject; and labeling the withdrawn RBCs with FDG to produce the FDG-RBCs.

In some embodiments, after blood is collected from a subject, and prior to incubation FDG, the RBCs are purified (separated) from one or more (optionally, all) of the other components of the collected blood, such as white blood cells (e.g., by differential centrifugation or flow cytometry).

The FDG and RBCs are incubated together under conditions that allow uptake of the FDG by the RBCs in sufficient amounts for PET. Appropriate incubation times and temperatures for sufficient FDG uptake by RBCs will depend upon the application. Incubation times within the range of 5 minutes to 120 minutes are appropriate for most applications. For example, a 5-minute incubation time may be used to test for occult gastrointestinal bleeding, as patients cannot wait for long periods of time to be imaged. This would require a larger amount of blood to be labeled as the FDG labeling efficiency will be lower, but should still be suitable for imaging. 120-minute incubations may be necessary for optimal internal labeling of RBCs, such as for tissue perfusion/ischemia imaging. Incubations in the experiments of the Examples herein were conducted at room temperature (approximately 25 degrees Celsius), and up to 37 degrees as indicated. In some embodiments, the incubation temperature for labeling is in the range of about 25 degrees to 37 degrees Celsius. However, other incubation temperatures could be utilized (e.g., plus or minus 1-5 degrees Celsius). For example, the incubation temperature can be in the range of 25 degrees to 42 degrees Celsius. In some embodiments, the incubation temperature is at least about 25 degrees Celsius, with an upper limit being a temperature that does not damage the RBCs and permits FDG uptake. In some embodiments, the incubation temperature is at least 37 degrees Celsius, with an upper limit being a temperature that does not damage the RBCs and permits FDG uptake. In a specific example, the incubation temperature is 37 degrees Celsius.

Optionally, the RBCs can be incubated with FDG in the presence of an agent that increases uptake of FDG by RBCs. In some embodiments, the agent is at least one of D-glucose, insulin, and adenosine triphosphate (ATP)D-glucose, insulin, and adenosine triphosphate (ATP).

Labelling of the RBCs can be carried out manually, or through automated equipment, or a combination.

In some embodiments, prior to introducing the FDG-RBCs, labeling of the RBCs comprises incubating the RBCs with FDG, and the method further comprises purifying the FDG-RBCs from incorporated (free) FDG prior to said introducing. Purification can be done by centrifugation and cell washing.

The labelled RBCs may be placed in a vessel or into a syringe for intravascular injection into the subject (such as the vein of an extremity or an artery).

In some embodiments, imaging comprises imaging a blood perfusion-dependent phenomenon. In some embodiments, the imaging comprises myocardial perfusion imaging (MPI) or cardiac contractility.

In some embodiments, the blood perfusion-dependent phenomenon is tissue ischemia or tissue perfusion. In some embodiments in which the blood perfusion-dependent phenomenon is tissue ischemia or tissue perfusion, the subject has suffered a stroke or undergone organ transplantation or tissue grafting.

In some embodiments, the blood perfusion-dependent phenomenon is internal bleeding.

In some embodiments, the imaging comprises imaging one or more sites of internal bleeding in the subject.

In some embodiments, the imaging is used for dynamic cardiac contractility assessment, or localization of sites of occult gastrointestinal bleeding.

In some embodiments, the blood-dependent phenomenon is tumor perfusion.

In some embodiments, the blood perfusion-dependent phenomenon is abnormal perfusion of the cerebral vasculature, such as in association with a neurodegenerative disease such as Alzheimer's disease.

In some embodiments, the imaging comprises combined positron emission tomography-computed tomography (PET-CT) imaging. For example, for detection of internal bleeding, combined PET-CT imaging with FDG-RBCs will likely be superior to PET imaging alone, as the co-registered CT images can give much better anatomic localization of bleeding sites. As the current official recommended imaging study (by the American College of Radiology) for evaluation of internal bleeding is contrast-enhanced CT, combined PET-CT imaging of FDG-RBCs can be utilized as an acceptable imaging alternative to contrast-enhanced CT.

In some embodiments, the subject into which the FDG-RBCs are introduced is a human.

In some embodiments, the subject into which the FDG-RBCs are introduced is a non-human animal.

In some embodiments, the RBCs internally labeled with FDG are autologous to the subject to which the FDG-RBCs are introduced (i.e., re-introduced).

In some embodiments, the RBCs internally labeled with FDG are allogeneic to the subject to which the FDG-RBCs are introduced.

In some embodiments, the RBCs internally labeled with FDG are xenogeneic to the subject to which the FDG-RBCs are introduced (e.g., human to animal, animal to human, or animal to animal).

In some embodiments, the RBCs are human RBCs. In some embodiments, the RBCs are rodent (e.g., mouse, rat, guinea pig), dog, cat, horse, cow, or pig RBCs. In some embodiments, the glucose analog is taken up by the RBCs via one or more GLUT transporters (e.g., GLUT1), and the non-human animal RBCs is one in which the corresponding GLUT transporter(s) is sufficiently expressed in the animal's RBCs to permit sufficient uptake by that mechanism (see Montel-Hagen A, et al., 2008).

The terms "subject," "individual," "host," and "patient" are used interchangeably herein to refer to a member or members of any multicellular organism, e.g., an animal, including mammalian and non-mammalian species, including human and non-human animals. Subjects and patients thus include, without limitation, humans, non-human primates, canines, felines, ungulates (e.g., equine, bovine, swine (e.g., pig)), avians, rodents (e.g., rats, mice), and other subjects. Non-human animals, e.g., non-human mammals, e.g., a non-human primate, a murine (e.g., a mouse, a rat), lagomorpha, etc. may be used for experimental investigations. Non-human animals may be imaged for veterinary medical purposes, or for research to model medical or veterinary disorders.

The FDG-RBCs may be introduced intravascularly into any part of the circulatory system including the pulmonary circulation, i.e., the "loop" or circuit through the lungs where the blood is oxygenated or into the systemic circulation, i.e., the "loop" or circuit through the rest of the body to provide oxygenated blood (e.g., intravenously or intraarterially), such as by injection or infusion.

The FDG-RBCs may be introduced in vitro or introduced into the blood circulatory system in vivo in an isolated form (separated from other components of the blood, such as WBCs), or in a composition that includes one or more, or all, components of the blood.

PET imaging is best performed using a dedicated PET scanner. However, it is possible to acquire PET images using a conventional dual-head gamma camera fitted with a coincidence detector. The quality of gamma-camera PET is considerably lower, and acquisition is slower. However, for institutions with low demand for PET, this may allow on-site imaging, instead of referring patients to another center, or relying on a visit by a mobile scanner.

The PET imaging can be a whole body scan of the entire circulatory system or any portion thereof, including pulmonary, systemic, or coronary, or an anatomical region in which abnormal bleeding can occur. In some embodiments, the PET imaging is cerebrovascular. Perfusion images (perfusion "maps") of an anatomical region of a subject with abnormal perfusion can be compared to perfusion images of the same or similar region in a subject with normal or abnormal perfusion or to the same subject from a previous imaging. In this way, the perfusion images can be used as a biomarker to detect the existence of a condition involving abnormal perfusion, or to monitor the condition's status (e.g., improvement or progression) such as in response to a treatment.

For example, images of cerebral vascular perfusion in a subject having, suspected of having, or at risk of having, a neurodegenerative disease such as Alzheimer's can be compared to an image of cerebral vascular perfusion of the same subject obtained previously or compared to that of a normal subject or to that of a subject having the neurodegenerative disease.

Another aspect of the invention concerns compositions useful for labeling RBCs with the 2-deoxy-2-($^{18}$F)fluoro-D-glucose (FDG). The composition includes FDG or is brought into contact with the RBCs in the presence of the FDG. In some embodiments, the composition comprises sodium chloride, potassium chloride, and one ore more of ethylenediaminetetraacetic acid (EDTA), heparin, or sodium citrate. Preferably, the composition is a solution when brought into contact with RBCs. In some embodiments, solution comprises 140 mM sodium chloride, 4 mM potassium chloride, and 2.5 mM EDTA (or equivalent of heparin or sodium citrate).

In some embodiments, the composition is a solution having a pH in the range of 7.0-7.7, such as pH of 7.4. In some embodiments, the composition further includes FDG. In some embodiments, the composition further includes an agent that increases uptake of FDG by RBCs, such as one or more of D-glucose, insulin, or adenosine triphosphate (ATP).

Another aspect of the invention concerns a kit for labeling RBCs. In some embodiments, the kit comprises sodium chloride; potassium chloride; and one or more of ethylenediaminetetraacetic acid (EDTA), heparin, or sodium citrate. These components may be in separate containers of suitable materials such as glass or plastic, or in a single container. In some embodiments, the kit comprises a composition of the invention useful for labeling RBCs (e.g., a labeling solution). The kit will include packaging.

In some embodiments, the kit further comprises FDG. The FDG is in a shielded container, which may be the same container as the sodium chloride, potassium chloride, and EDTA/heparin/sodium citrate, or a separate container. Shielded containers are constructed of appropriate materials for radiation protection, such as lead and steel.

In some embodiments, the kit further includes an agent that increases uptake of FDG by RBCs, such as one or more of D-glucose, insulin, or ATP.

The kit may further include instructions for use of the kit components for labeling RBCs, e.g., for use in an embodiment of the methods of the invention. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form would be a computer readable medium, e.g., CD, DVD, BLU-RAY, flash memory, etc., on which the information has been recorded. Yet another form that may be present is a website address which may be used via the Internet to access the information at a removed site. Any convenient form may be present in the kits.

Clinical blood pool imaging is often performed in nuclear medicine facilities with 99m-Technetium-labeled agents, primarily human red blood cells (i.e., the "99m-Tc tagged RBC scan"). While several PET-based blood perfusion agents have been introduced, these have found limited application, and are seldom used as blood pool agents. Given the high physiologic expression of the GLUT1 transporter on human RBCs, the inventor hypothesized that human RBCs can spontaneously internalize the widely available PET tracer 18F-FDG in vitro and serve as a PET blood pool agent in an immunodeficient mouse model.

250 µl human RBCs (Zen-Bio) were washed with sterile "1×EDTA" solution (140 mM NaCl, 4 mM KCl, 2.5 mM K$_2$EDTA.2H$_2$O), mixed with 370-740 MBq USP grade 18F-FDG (Cardinal Health) 37° C. 30', centrifuged 1000 g 10', and washed twice in 4× volume 1×EDTA solution. FDG-labeled RBCs were resuspended in 250 µl 1×EDTA solution. Sample/wash aliquots were counted in an Atomlab 600 dose calibrator (Biodex) to measure % retained FDG.

4-6 wk old splenectomized NSG immunodeficient mice (Jax Lab) were fasted O/N and phlebotomized (200-250 µl), prior to microPET imaging with an INVEON PET/CT preclinical scanner (Siemens). Mice were injected with 500 µl FDG-labeled RBCs via tail vein. ECG-gated raw PET data were acquired 10' in list-mode format, followed by CT attenuation correction scan.

PET images were analyzed with INVEON workstation software (Siemens). Patlak compartment plot option was chosen. For 3D PET and 4D PET data sets, VOIs were selected manually based on corresponding CT images: heart, leg muscle, liver, kidney and brain. Voxel activities were represented in standard uptake values (SUV).

Results are shown in the Examples and figures. The results show that human RBCs can rapidly incorporate sufficient amounts of FDG to obtain in vivo images of the mouse vasculature using microPET/CT. As modern clinical PET/CT scanners generally possess count detection sensitivities far higher than that of clinical gamma scintigraphic cameras, FDG-RBC PET imaging may achieve comparable results to $^{99m}$Tc-based blood pool imaging, with a potentially significant overall reduction in patient radiation dose. This technique can have other clinical PET blood pool/perfusion applications as well.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—2-Deoxy-2-($^{18}$F)Fluoro-D-Glucose (FDG) Labeling of Human Red Blood Cells (RBCs)

The purpose of this project is to determine whether human red blood cells (RBCs) can incorporate a significant amount of 18F-Fluorodeoxyglucose (FDG). In vivo imaging of FDG-labeled RBCs (FDG-RBCs) using PET-CT offers potentially significant advantages over the current clinical SPECT imaging tests that utilize 99-Tc labeled RBCs, namely significantly higher radiolabel count detection rates/unit of time (~300-1000× higher), as the count detection sensitivity of PET is ~100-300 fold higher than SPECT (Rahmin and Zaidi, 2008), and 18-Fluorine $t_{1/2}$ is 3× shorter than 99-Tc (110 minutes vs. 360 minutes).

Resuspension and Incubation Protocol:
1. Re-suspend 150 µl of washed packed human RBCs (hRBCs; 150 µl≈3×10$^8$ hRBCs) (Purchased from vendor Zen-Bio) in each of 3 different solutions:
   a. 1.2 ml of "Citrate" solution: 140 mM NaCl, 4 mM KCl, 1.25 mM sodium citrate dihydrate (pH 7.2 with NaOH/HCl)
   b. 1.2 ml of "EDTA" solution: 140 mM NaCl, 4 mM KCl, 2.5 mM K$_2$EDTA dihydrate
   c. 1.2 ml of "Heparin" solution: 140 mM NaCl, 4 mM KCl, 1 U Heparin
2. Incubate 37 degrees C. for 3 hours (step to accelerate both endogenous glucose depletion and glucose efflux)
3. Centrifuge each sample 500 g 10'; remove supernatant; re-suspend RBC pellet in 30-90 µCi of FDG (Cardinal Health); discard supernatant
4. Bring each RBC sample to final volume of 1 ml of original solution (Citrate, EDTA, or Heparin)
5. Incubate room temperature (RT) for 1 hour
6. Gently re-suspend RBCs and then remove 300 µl of RBC solution
   a. Spin 300 µl aliquot at 500 g 10' RT; remove supernatant into separate Eppendorf/collection tube; count FDG activity of cell pellet and supernatant against control FDG sample
7. Incubate RT another hour (2 hour time point)
   a. Gently re-suspend RBCs; Spin 300 µl aliquot at 500 g 10' RT; remove supernatant into separate Eppendorf/collection tube; count FDG activity of cell pellet and supernatant against control FDG sample
8. Incubate RT another hour (3 hour time point)
9. Gently re-suspend RBCs; Aliquot 300 µl; spin 500 g 10' RT; remove supernatant into separate Eppendorf/collection tube; count FDG activity of cell pellet and supernatant against control FDG sample.

Figure 2:
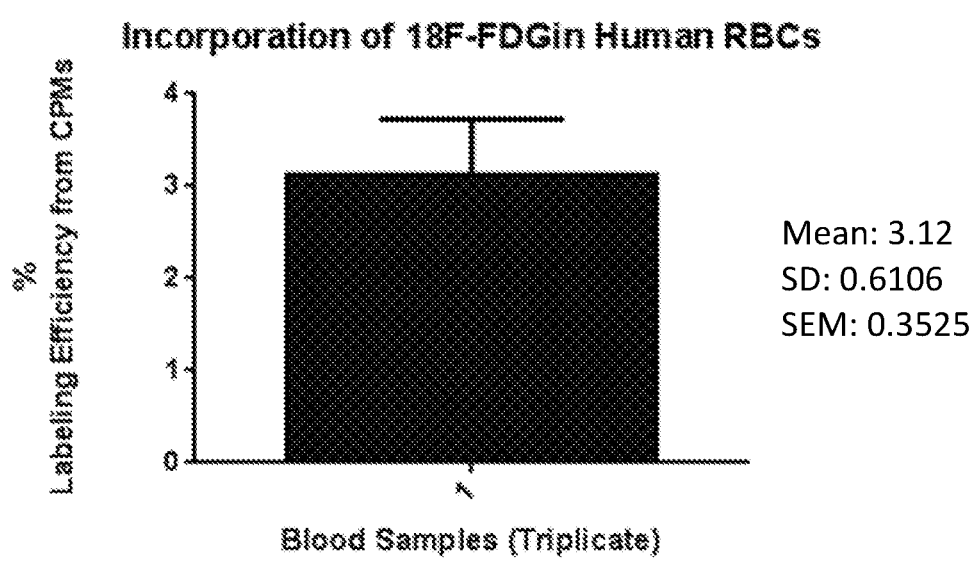
FIG. 2 shows a graph summarizing incorporation of FDG into human RBCs.
Figure 3:
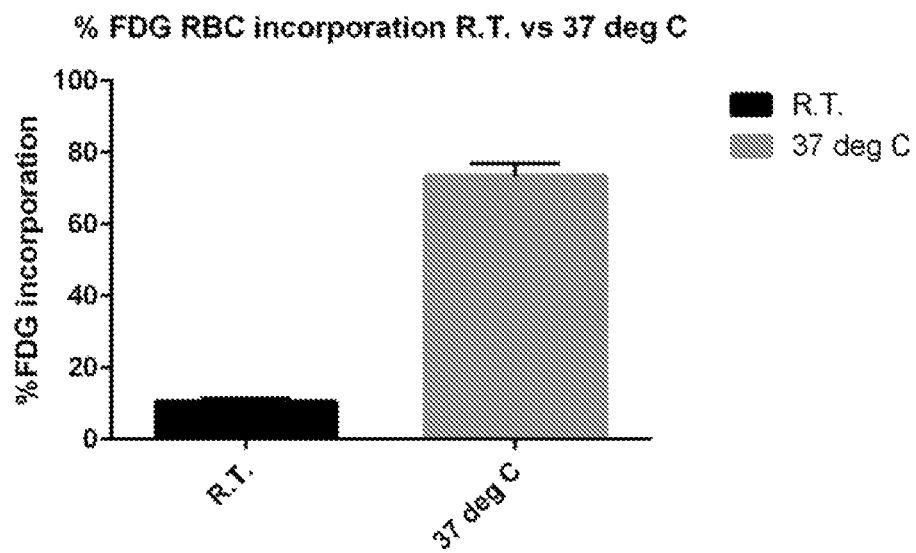
FIG. 3 shows physiologic FDG uptake by human RBCs is dependent on FDG incubation temperature. The percent FDG uptake by human red blood cells is significantly lower at room temperature ("R.T." ~25° C.) vs. 37° C. 250 µl of 1 day old human RBCs were incubated with 100 µl (1 milliCurie) 18F-FDG for 2 hours. Y axis: % total FDG incorporation. Mean values±SEM: R.T.=10.3%±1.1%, N=9; 37° C.=73.3%±3.6%, N=8. Unpaired t test P value <0.001; $R^2$=0.953.

FDG-RBC Labeling:
150 microCuries of FDG in a 100 microliter volume was incubated with 250 microliters of human red blood cells to a final solution volume of 500 microliters (NaCl/KCl/EDTA solution contains 140 mM NaCl, 4 mM KCl, 2.5 mM K$_2$EDTA dihydrate). FDG incubation duration=5 minutes at room temperature. Triplicate samples were used. Samples were centrifuged 1000 g 10 minutes after 5 minute FDG incubation, and RBC pellet was washed twice with 1.0 ml of NaCl/KCl/EDTA solution. A sample of the collected supernatant and a pellet sample was counted in a gamma counter with 18-F gating. 3% incorporation rate=4.5 microCurie of incorporated FDG/250 microliters of human red blood cell=18 microCurie of FDG/1 ml human red blood cells. Thus, 60 milliliters of whole blood from a patient should yield approximately 432-486 microCuries of FDG labeled red blood cells. (Assumes average 40% female hematocrit and 45% male hematocrit). Results are shown in FIG. 2.

Example 2—Injection of Mice with FDG and FDG-RBC

Approximately 47 microCuries of FDG-labeled human erythrocytes were injected via tail vein catheter into a splenectomized NSG immunodeficient mouse. The mouse was placed into a Siemens INVEON microPET scanner, and 18-F PET imaging of the mouse was performed over a 20-minute time period. FIG. 1A shows the resulting PET image, with the top of the image depicting the mouse tail and the bottom of the image depicting the mouse head.

Figure 1B:
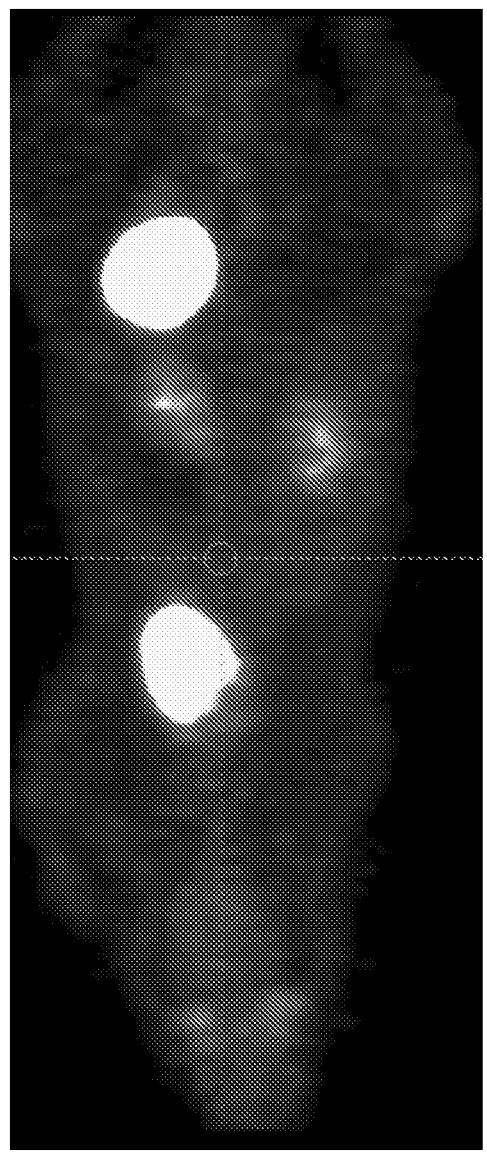
FIG. 1B: shows the PET image of a splenectomized NSG immunodeficient mouse following injection of approximately 32 microCuries of free FDG via tail vein catheter. The top of the image shows the mouse tail and the bottom of the image shows the mouse head. The green circular region of interest marker is placed over the expected location of the abdominal vessels. The majority of free FDG uptake is seen in the heart muscle, bladder, and kidneys, with faint activity over the brain.

Approximately 32 microCuries of free FDG were injected via tail vein catheter into a second splenectomized NSG immunodeficient mouse. The mouse was placed into the Siemens INVEON microPET scanner, and 18-F PET imaging of the mouse was performed over a 20-minute time period. FIG. 1B shows the resulting PET image, with the top of the image depicting the mouse tail and the bottom of the image depicting the mouse head.

The expected better count sensitivity and spatial resolution of FDG-RBC based PET imaging may yield results that lead to clinically significant improvements in the treatment and management of human patients with occult gastrointestinal bleeding compared to 99-Tc RBC SPECT imaging. FDG-RBC PET imaging may also have potential advantages over the Multi Gated Acquisition Scan (MUGA) currently used for monitoring chemotherapy-related cardiac toxicity in cancer patients, either through significantly shorter scan times and/or a significantly lower cardiac radiation dose.

Example 3—Using 18F-FDG Labeled Human Erythrocytes as a PET Blood Pool Imaging Agent in an Immunodeficient Mouse Model 99m-Technetium-labeled ($^{99m}$Tc) red blood cell imaging with planar scintigraphy is widely used in the clinical setting, primarily for the evaluation of patients with occult gastrointestinal bleeding ("$^{99m}$Tc-tagged red blood cell scan") and for the cardiac evaluation of patients at risk for chemotherapy-induced cardiotoxicity (Multiple Gated Acquisition or "MUGA" scan). While a number of alternative radionuclide-based blood pool imaging agents have been proposed, none of these have yet to achieve widespread clinical use. Presented herein is both in vitro and small animal in vivo imaging evidence suggesting that the high physiological expression of the GLUT1 transporter on human erythrocytes allows for erythrocyte uptake of the PET tracer 2-deoxy-2-($^{18}$F)fluoro-D-glucose (FDG) at a rate and magnitude amenable for clinical blood pool PET imaging. This imaging technique is likely to be amenable to rapid clinical translation, as it can be achieved using a simple FDG incubation protocol, requires a relatively small volume of phlebotomized blood, and can be completed within a relatively short time period. As modern PET scanners typically have much greater count detection sensitivities than that of commonly used clinical gamma scintigraphic cameras, FDG-labeled human erythrocyte PET imaging may not only have significant advantages over the $^{99m}$Tc-labeled red blood cell scan in its commonly used indications, but may also potentially have other clinical blood pool/blood perfusion imaging applications.

Clinical blood pool imaging is commonly performed in nuclear medicine departments using autologous human red blood cells (RBCs) labeled with the radiotracer 99m-Technetium pertechnetate, using gamma scintigraphic imaging (i.e., the "tagged RBC scan"). The two main common clinical indications for the $^{99m}$Tc-labeled red blood cell scan are 1) the detection of drug-induced cardiomyopathy in cancer patients undergoing potentially cardiotoxic chemotherapy (MUGA scan), and 2) anatomic localization of sites of occult lower intestinal bleeding in patients (Burow et al., 1977; Thorne et al., 1987; Wang et al., 2015).

As modern clinical PET/CT scanners have significantly greater count detection sensitivities, as well as greater spatial and temporal resolution over typical clinical planar scintigraphic cameras and certain SPECT platforms, the development of PET-based blood pool imaging agents remains of great interest (Rahmim and Zaidi, 2008). A number of PET specific radiotracers have been investigated as blood pool imaging agents, but are not yet available for clinical use (Niu et al., 2014; Basuli et al., 2015; Saatchi et al., 2012). There are a few PET-based blood perfusion agents based on 15-Oxygen-labeled ($^{15}$O) compounds such as $H_2{}^{15}O$ that are clinically available, but are unlikely to achieve wide-spread clinical adoption, as the very short radioactive half-life of $^{15}$O (≈2 minutes) requires the presence of a cyclotron within close proximity to the PET scanner (de Langen, 2008; Fan et al., 2016; Ibaraki et al., 2008; Lodge et al., 2008). Other PET or SPECT blood perfusion agents have either a narrowed or incompletely characterized range of application, such as 62-Copper-pyruvadehyde-bis($N^4$-methylthiosemicarbazone) ($^{62}$Cu-PTSM), 68-Gallium-labeled microspheres, or the $^{99m}$Tc-labeled cerebrovascular perfusion agents hexamethylpropyleneamine oxime (HMPAO) and ethylcysteinate dimer (ECD) (Green et al., 1988; Shelton et al., 1990; Welch et al., 2000; Haynes et al., 2000; Wong et al., 2008; Zhang et al., 2013; Flower et al., 2001; Green et al., 1990; Wallhaus et al., 2001; Herrero et al., 1996; Bailey et al., 2016; Bonte, et al., 2011; Goffin et al., 2008).

The inventor hypothesized that human RBCs can physiologically internalize a relatively large amount of the PET tracer 18F-FDG that would be sufficient for PET-based in vivo RBC imaging, for a few reasons: 1) Of all cells in the human body, human RBCs have the highest level of expression of the glucose transporter GLUT1, with each RBC expressing roughly 2-3×10$^5$ copies of GLUT1 on the plasma membrane, 2) Human RBCs also express other glucose transporters, albeit at lower levels, including GLUT4 and Sodium-glucose co-transporters, and 3) Intracellular glucose concentrations in human RBCs are normally high, as it mirrors that of human blood (4-6 mM) (Montel-Hagen et al., 2008; Viskupicova et al., 2015).

Presented herein is evidence that human RBCs can be sufficiently labeled with FDG to acquire whole body images of the vasculature of splenectomized immunodeficient NSG mice using a microPET/CT scanner. In addition, the cell labeling technique is straightforward to perform and can be completed in a relatively short time period.

Materials and Methods:

Human red blood cell (RBC) preparation and FDG-RBC labeling: Packed human red blood cells collected in standard anticoagulant citrate dextrose (ACD) solution (either ≤24 hours post phlebotomy or ~5 day post phlebotomy) were obtained from Zen-Bio, Inc. 370-740 Megabecquerel (MBq) (1 ml) USP grade 2-deoxy-2-($^{18}$F)fluoro-D-glucose (FDG) were obtained from Cardinal Health. Vendor supplied human RBCs are centrifuged 1000 g 10', and the remaining anticoagulant and buffy coat residual are gently aspirated. RBCs are then gently washed in a 4× volume of filter sterilized "1×EDTA" solution (140 mM NaCl, 4 mM KCl, 2.5 mM Ethylenediaminetetraacetic acid dipotassium salt dihydrate ($K_2$EDTA dihydrate)), centrifuged at 1000 g 10', and the wash is manually aspirated. 150 µl 1×EDTA solution is then added to the 250 µl washed RBCs and 100 µl (37-74 MBq) FDG to a final volume of 500 µl. For experiments using 500 µl packed RBCs, 400 µl 1×ETDA solution and 100 µl (37-74 MBq) FDG are added to a final volume of 1000 µl. Samples are then gently rotated at either room temperature (~25° C.) for 2 hours or at 37° C. for 30 minutes. Samples are then centrifuged at 1000 g 10' and the supernatant is carefully aspirated. RBCs are then washed and centrifuged twice with 4× volumes of 1×EDTA solution. For experiments characterizing residual unincorporated FDG, a 3$^{rd}$ wash/centrifugation step was performed. Final washed FDG-labeled RBCs are resuspended in 1× volume of 1×EDTA solution. Aliquots from all samples and washes are counted with the Atomlab™ 600 dose calibrator (Biodex Medical Systems, Inc.).

RBC membrane integrity assay: 740 MBq (1 ml) USP grade FDG (Cardinal Health) was allowed to decay for 14 days prior to use as "cold" FDG. Human RBCs (<24 hours post phlebotomy) were incubated with cold FDG, using the protocol previously described. Diluted aliquots of RBCs after each centrifugation step were stained with Trypan Blue dye and samples were counted to determine relative % RBCs with intact membranes.

ECG-gated whole body microPET imaging of NSG immunodeficient mice: 4-6 week old splenectomized NOD scid gamma (NSG™) immunodeficient mice were obtained from The Jackson Laboratory. Mice were placed in specialized housing for immunodeficient mouse in the Moffitt Cancer Center (MCC) vivarium. Approval for all animal experimentation was first obtained from the University of South Florida (USF) Institutional Animal Care and Use Committee (IACUC). All animal experimentation was performed in accordance to federal regulations and USF IACUC principles and procedures. Animal imaging was performed in the MCC Small Animal Imaging Laboratory with an INVEON PET/CT (Siemens Medical Inc., Knoxville, Tenn.) preclinical scanner. Mice are first fasted the night before microPET imaging and undergo phlebotomy of ≈200-250 µl whole blood via retro-orbital venous plexus puncture immediately prior to microPET imaging. Blood glucose from the phlebotomized blood is measured. A tail vein microcatheter is placed in each mouse under inhalational isoflurane anesthesia. Mice are maintained under inhalational anesthesia and immobilized on the microPET platform before injection of 500 µl of FDG-labeled RBC solution through the tail vein catheter. The PET part of the system has 64 detector blocks with total field of view (FOV) 12.7 cm and a spatial resolution of 1.4 mm. Raw PET data were acquired for 10 minutes in a list-mode data format, followed by CT attenuation correction scan. Imaging started immediately after tail-vein injection of 18F-FDG infused RBCs. The ECG signal in each mouse was detected with three flat electrodes placed in two front and one rear limbs of each animal (ground lead on a rear leg). The signals detected by these electrodes were recorded during 10 minutes time period by BIOVET® (m2m Imaging) physiological monitoring and heating system. The threshold for TTL cardiac gating signals was set in a rising mode of R-wave peak. The PET list-mode data were reconstructed using 3D-OSEM iterative algorithm with four iterations and eight subsets, with a final image volume of 256×256×256 voxels. Voxel effective dimensions were 1.4×1.4×1.4 mm. For each animal there are three data sets: standard 3-dimensional (3D) PET reconstruction, resulting in a motion-time average 3D PET image; dynamic 3D PET reconstruction with 30 frames; and the phase-based 4-dimensional (regular 3-dimensional plus time, 4D) PET cardiac reconstruction, with four cardiac gates binning. In all cases, CT attenuation correction was applied to the PET images.

PET images of the mice were analyzed using INVEON Workstation Software (Siemens Medical Inc., Knoxville, Tenn.). Vendor software-supplied Patlak compartment plot option was selected (Patlak et al., 1983). For 3D PET and 4D PET data sets multiple volumes of interest (VOI) were selected manually based on corresponding CT images including: heart, leg muscle, liver, kidney and brain. Voxel activities were represented in standard uptake values (SUV). Dynamic activity curves were plotted for VOIs using dynamic 3D PET data set for each animal. The 4D PET data were used for defining cardiac function. First the heart was segmented on CT images based on anatomical features, after that segmented volume (cardiac PET VOI) was transferred into co-registered PET images.

Figure 4:
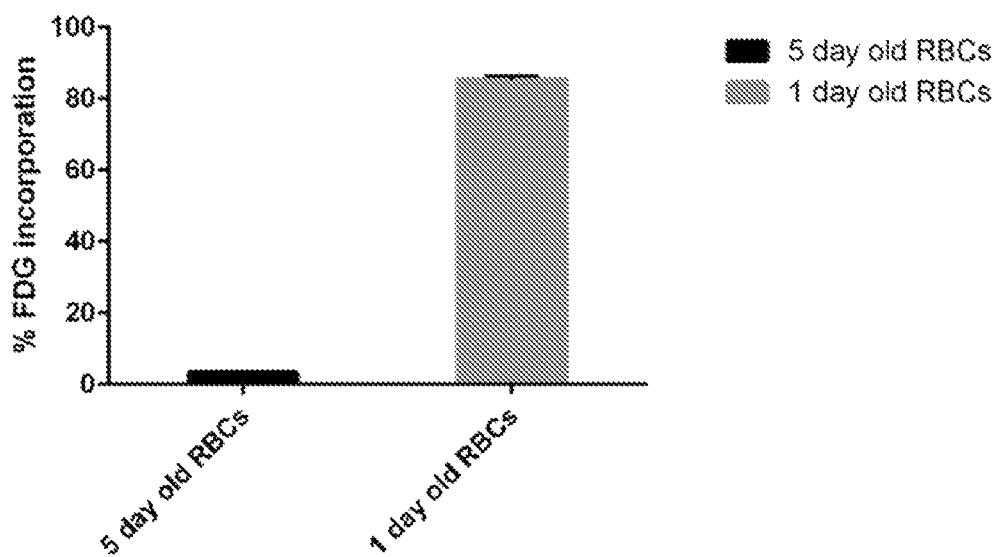
FIG. 4 shows the relative percent FDG uptake by 5 days old human red blood cells (post-phlebotomy) vs. 1 day old human red blood cells. Either 250 µl of 1 day old human RBCs or 5 day old RBCs were incubated with 100 µl (≈37 MBq) 18F-FDG for 2 hours. Y axis: % total FDG incorporation. X axis: 5 vs 1 day old RBCs (mean values±SEM). Physiologic FDG uptake by human RBCs is dependent on RBC age post phlebotomy. The percent FDG uptake by 5 days old human red blood cells (post-phlebotomy) is significantly lower than 1 day old human red blood cells. Mean values±SEM: 5 day old RBC=3.3%±0.2%, N=3; 1 day old RBC=85.3%±1.8%, N=3. Unpaired t test P value <0.001; $R^2$=0.998.

Results:

FDG Uptake by Human RBCs is Dependent on Age of Cells after Phlebotomy:

The percent of FDG uptake by human erythrocytes collected ≤24 hours prior to FDG labeling was significantly higher than that of RBCs collected≈5 days prior to FDG labeling (FIG. 4). The mean % total FDG incorporation of 250 µl of 1 day old RBCs (30' 37° C. incubation with 37-74 MBq FDG) was 85.3%±1.8%, compared to 3.3%±0.2% FDG incorporation of 5 day old RBCs (N=3). Unpaired t test P value <0.001; $R^2$=0.998.

FDG Uptake by Human RBCs is Dependent on FDG Incubation Temperature:

The % total FDG incorporation of 250 µl of 1 day old human RBCs incubated with 37-74 MBq FDG for 2 hours at room temperature (≈25° C.)=10.3%±1.1% (N=9), compared to =73.3%±3.6% when FDG RBC incubation was performed for 30' at 37° C. (N=8). Unpaired t test P value <0.001; $R^2$=0.953.

Figure 5:
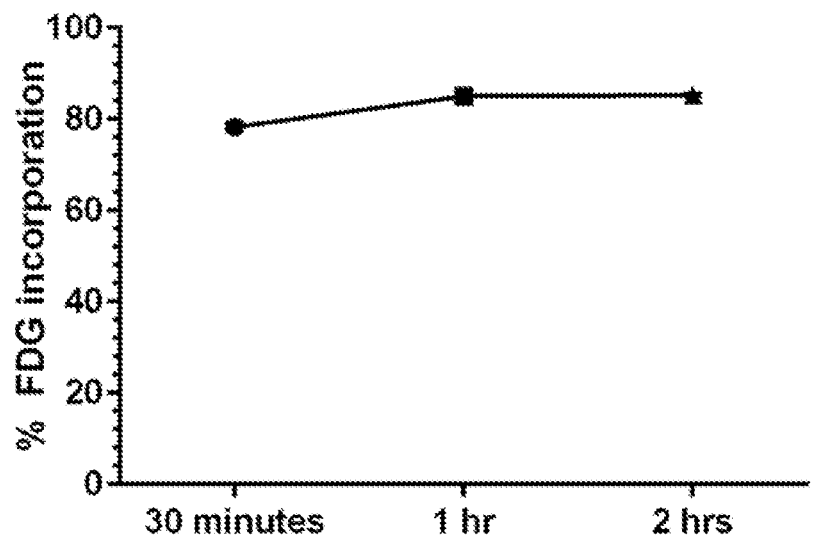
FIG. 5 shows 250 µl of 1 day old human RBCs were incubated with 100 µl (≈37 MBq) 18F-FDG at 37° C. for 30 minutes, 1 hour, or 2 hours. Y axis: % total FDG incorporation. N=3/timepoint. X axis: incubation time (mean values±SEM). Maximum RBC incorporation of FDG at 37° C. is nearly complete by 30 minutes. Mean values±SEM: 30 minutes=78.3%±0.9; 1 hour=85.0%±0.0%; 2 hours=85.3%±0.3%.
Figure 6:
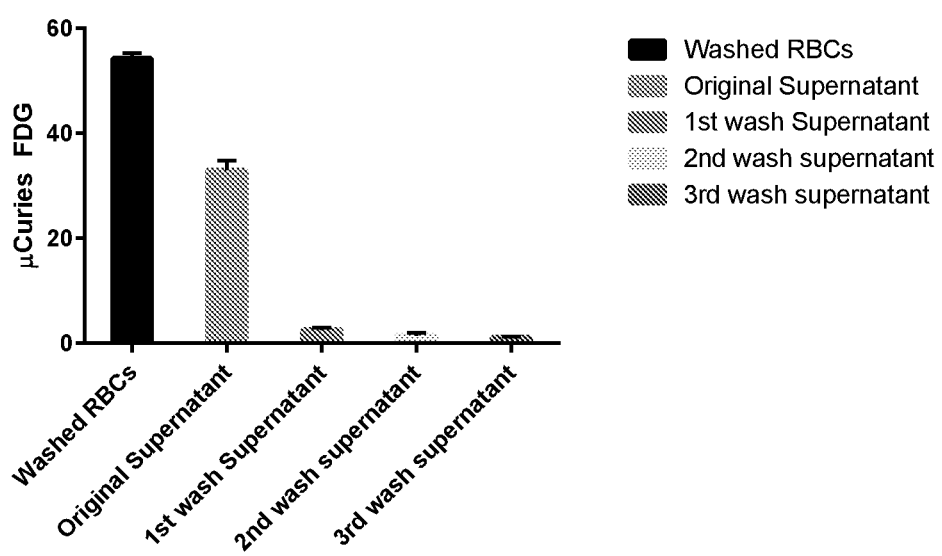
FIG. 6 shows minimal residual free FDG remains in RBC fraction after first RBC wash. There is minimal residual free FDG remaining in the FDG-labeled RBC fraction after the $1^{st}$ wash (≈FDG activity in $2^{nd}+3^{rd}$ washes) 3.1% of total FDG (avg). Y axis=µCuries FDG. N=4/column. FDG µCuries Mean values±SEM: Washed RBC's=54.3±1.0; Original supernatant (unincorporated FDG)=33.0±1.8; $1^{st}$ wash supernatant=2.6±0.4; $2^{nd}$ wash supernatant=1.5±0.5; $3^{rd}$ wash supernatant=1.1±1.2. Based on these results, a single wash step is expected to be sufficient for clinical trial purposes.
Figure 7:
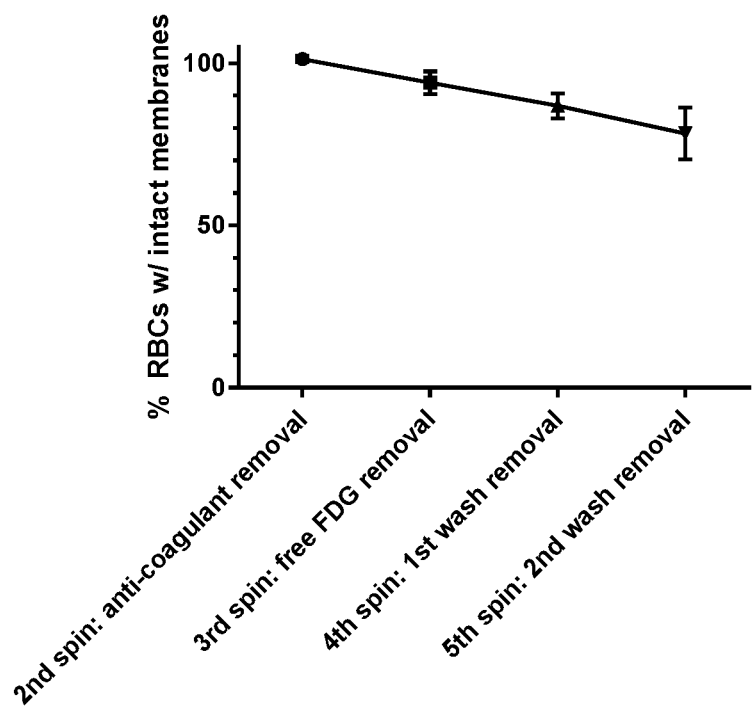
FIG. 7 shows slow decline in % labeled RBC's with intact cell membranes after each centrifugation step. The relative % of labeled RBC's with intact cell membranes was measured after each centrifugation step of the FDG labeling protocol, using trypan blue exclusion staining and cell counting. $1^{st}$ spin: (baseline=prior RBC isolation/centrifugation by vendor (Zen-bio)); $2^{nd}$ spin: After anti-coagulant removal from vendor purified RBC's; $3^{rd}$ spin: After removal of unincorporated free FDG post 30 minute FDG incubation at 37° C.; $4^{th}$ spin: After removal of $1^{st}$ EDTA buffer wash from FDG-labeled RBC's; $5^{th}$ spin: After removal of $2^{nd}$ EDTA buffer wash from FDG-labeled RBC's. NOTE: Future clinical application of this protocol eliminates "$2^{nd}$ spin" centrifugation step, as initial RBC isolation and anti-coagulant removal are to be combined into single centrifugation step, likely reducing final RBC damage. Y axis=% of total RBC's. N=3/step. Values are normalized to baseline % vendor-supplied isolated RBCs with intact membranes (i.e., post $1^{st}$ spin). Mean values±SEM: $2^{nd}$ spin=101.2%±1.0%; $3^{rd}$ spin=93.9%±3.5%; $4^{th}$ spin=86.8%±3.9%; $5^{th}$ spin=78.3%±8.0%.
Figure 8:
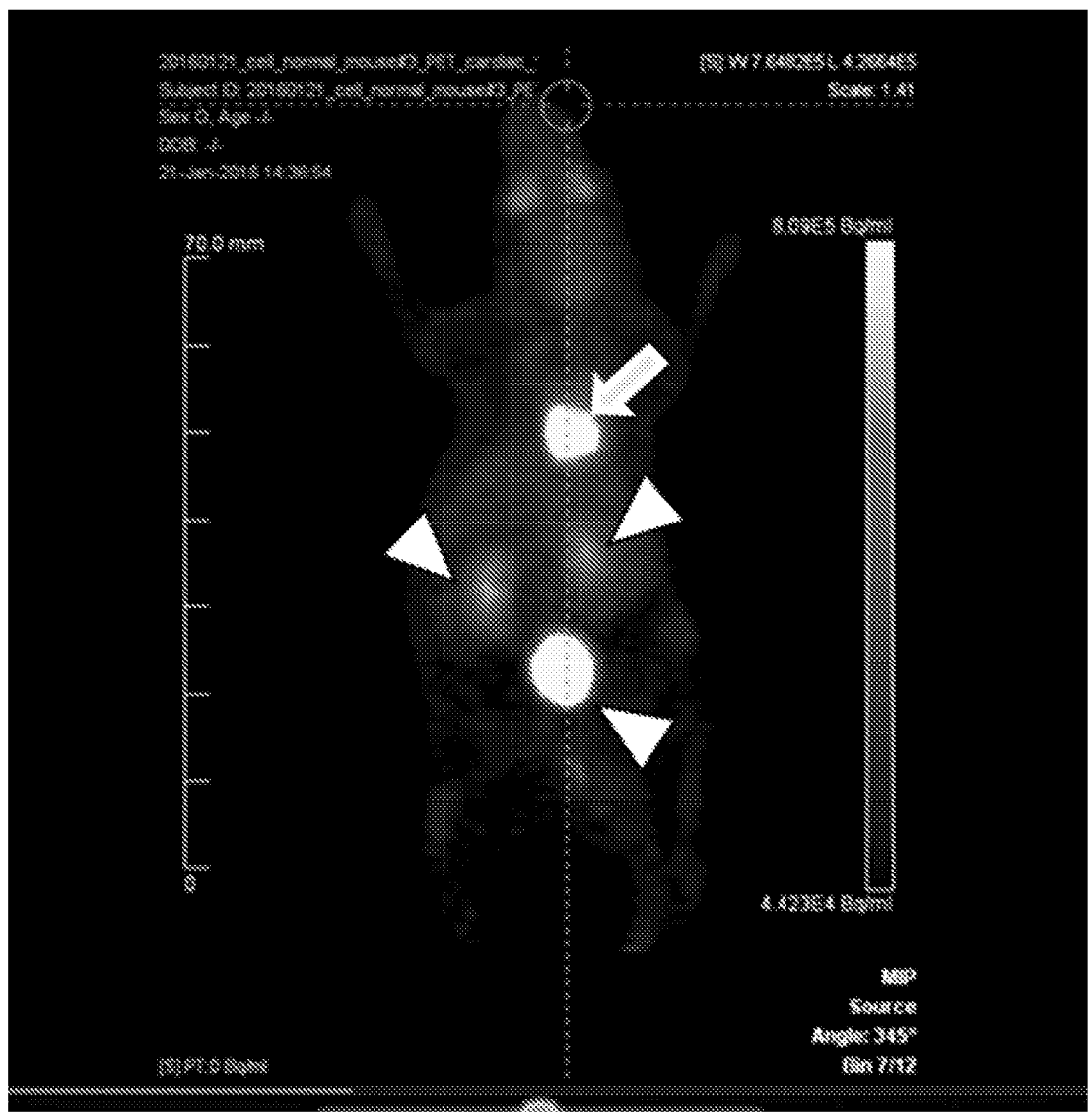
FIG. 8 and FIG. 9 show in vivo ECG-gated microPET imaging of free FDG vs. 18F-FDG-labeled human RBCs in splenectomized NSG immunodeficient mice.
Figure 9:
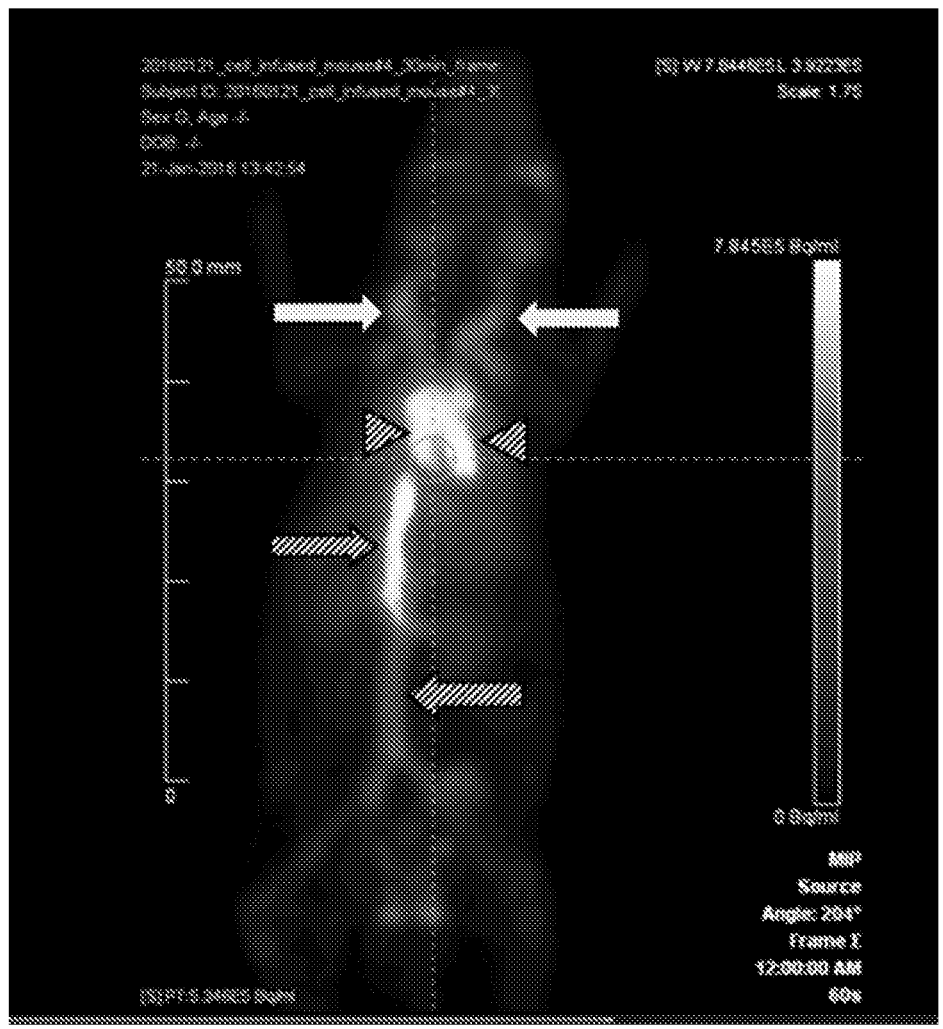

Maximum Human RBC Incorporation of FDG at 37° C. is Nearly Maximum by 30 Minutes:

The % total FDG incorporation of 250 µl of 1 day old human RBCs incubated with 37-74 MBq FDG at 37° C.=78.3%±0.9 at 30 minutes, 85.0%±0.0% at 1 hour, and 85.3%±0.3% at 2 hours (FIG. 5; N=3).

Figure 14:
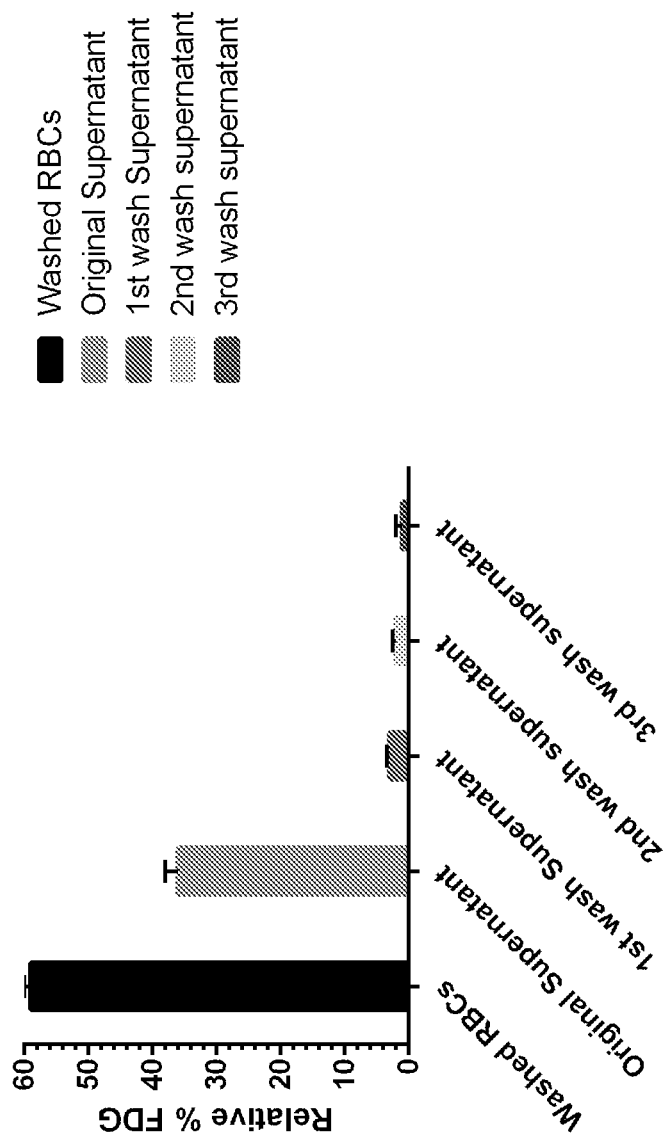
FIG. 14: Relative % free FDG remaining in the FDG-labeled RBC fraction (250 µl), original incubation supernatant, and wash supernatants. Y axis=% free FDG. X axis: cells or supernatants (mean±SEM).

Minimal Residual Unincorporated FDG Remains in Washed RBC Samples after First Wash Step:

The FDG activity in the washed cell samples, original incubation solution, and subsequent 3 washes was measured and the relative % of total FDG were as follows: Washed RBC fraction (500 µl)=59%±1%; Original supernatant (unincorporated FDG after initial incubation)=36%±2%; $1^{st}$ wash supernatant=3%±1%; $2^{nd}$ wash supernatant=2%±1%; $3^{rd}$ wash supernatant=1%±1% (FIG. 14).

Slow Gradual Decline in % FDG-Labeled RBCs with Intact Cell Membranes is Seen after Each Centrifugation Step:

The relative % of labeled RBC's with intact cell membranes was measured after each centrifugation step of the FDG labeling protocol, using trypan blue exclusion staining and cell counting. A slow gradual decline in % of FDG labeled cells with intact cell membranes is seen after each centrifugation step, as follows: After anti-coagulant removal from vendor purified RBC's≈100%±1.0%; After removal of unincorporated free FDG post 30 minute FDG incubation=93.9%±3.5%; After removal of $1^{st}$ wash from FDG-labeled RBC's=86.8%±3.9%; After removal of $2^{nd}$ wash from FDG-labeled RBC's=86.8%±3.9% (N=3).

Figure 15B:
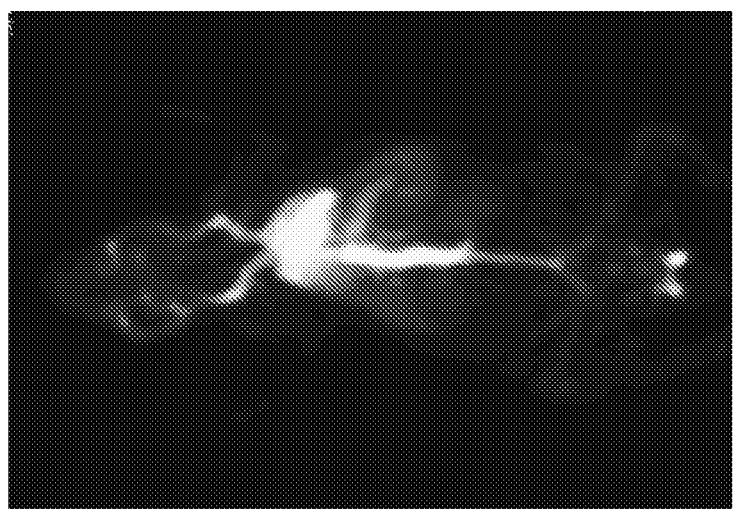
FIGS. 15A and 15B.
Figure 15A:
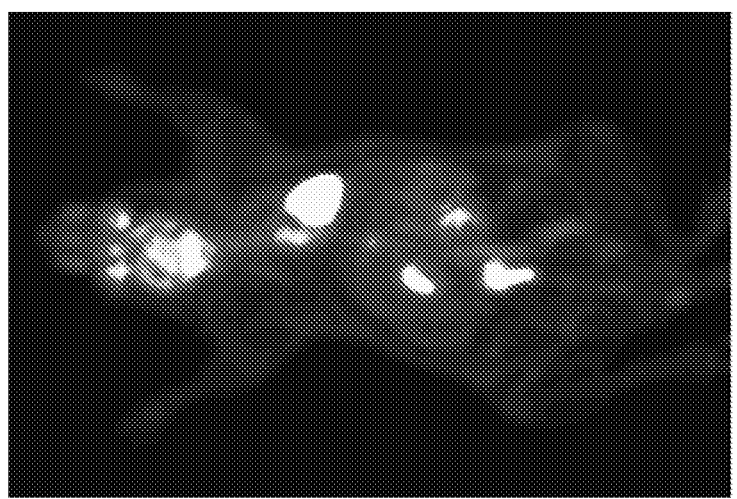

In Vivo ECG-Gated microPET Imaging of Splenectomized NSG Immunodeficient Mice Injected with FDG-Labeled Human RBCs Allows Visualization of the Vasculature of the Mouse Body:

Splenectomized NSG immunodeficient mice were injected with 1.7-10.4 MBq FDG-labeled RBCs or 1.4-1.8 MBq of FDG (N=4/group) and underwent ECG-gated microPET/CT imaging. Whole body microPET images of FDG-labeled RBC injected mice show that the FDG activity is largely confined to the large vessels of the mouse body. Activity over the heart is also seen, as well as perfusion of the lungs, liver, spleen, kidneys, and the testes in male mice (FIG. 15B). Activity could also be visualized within smaller caliber vessels, such as the carotid arteries in the central neck. FDG activity within the kidneys of these mice demonstrates a vascular distribution pattern, unlike the accumulation of excreted FDG in the renal pelvises of control mice injected with free FDG. In addition, a small amount (<5%) of total body FDG activity was seen overlying the bladder in mice injected with FDG-labeled RBCs, consistent with small urinary excretion of residual free/released FDG in these mice over the observed time period. There was also a relative paucity of FDG activity in the brain of these mice. By contrast, the biodistribution of free FDG in control mice demonstrates expected intense FDG accumulation in the myocardium and brain, as well as marked urinary excretion in the kidneys and bladder (FIG. 15A).

Figure 10:
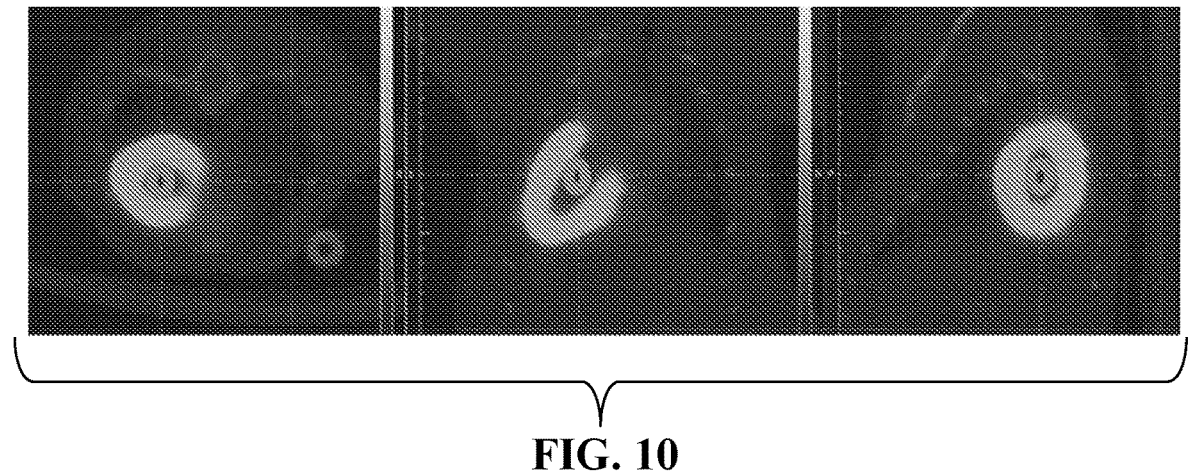
FIG. 10 and FIG. 11: In vivo ECG-gated microPET imaging of the heart of NSG mice injected with free FDG vs. 18F-FDG-labeled human RBCs.
Figure 11:
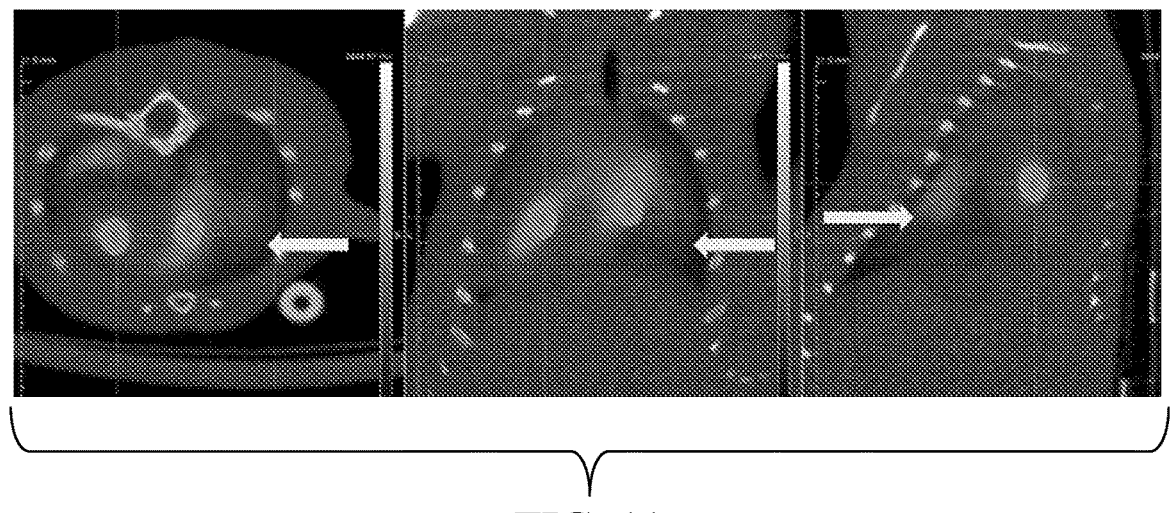
Figure 12:
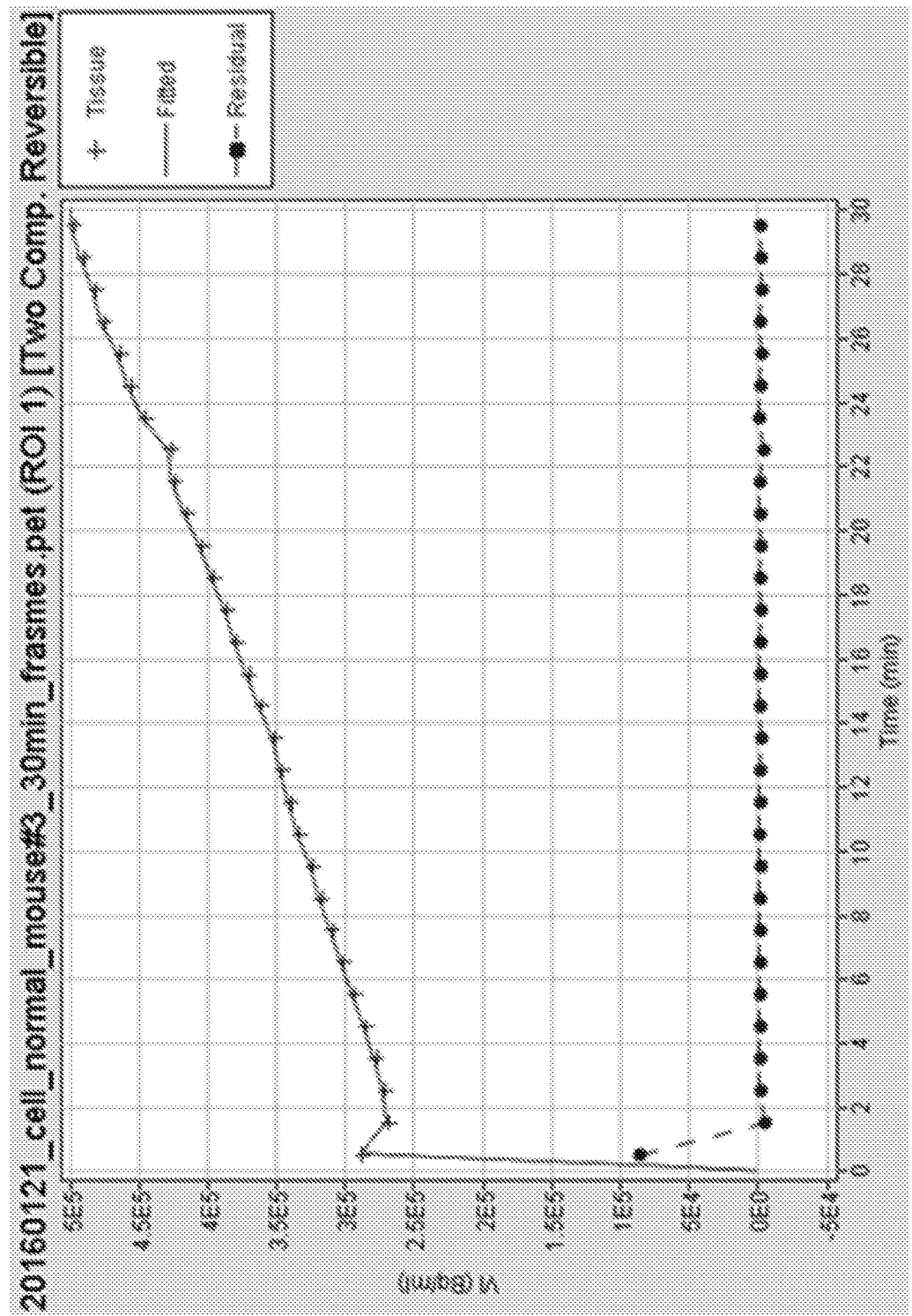
FIG. 12 and FIG. 13: FDG Time activity curve (TAC) of the mouse heart for FDG-labeled RBCs matches that expected of blood pool.
Figure 13:
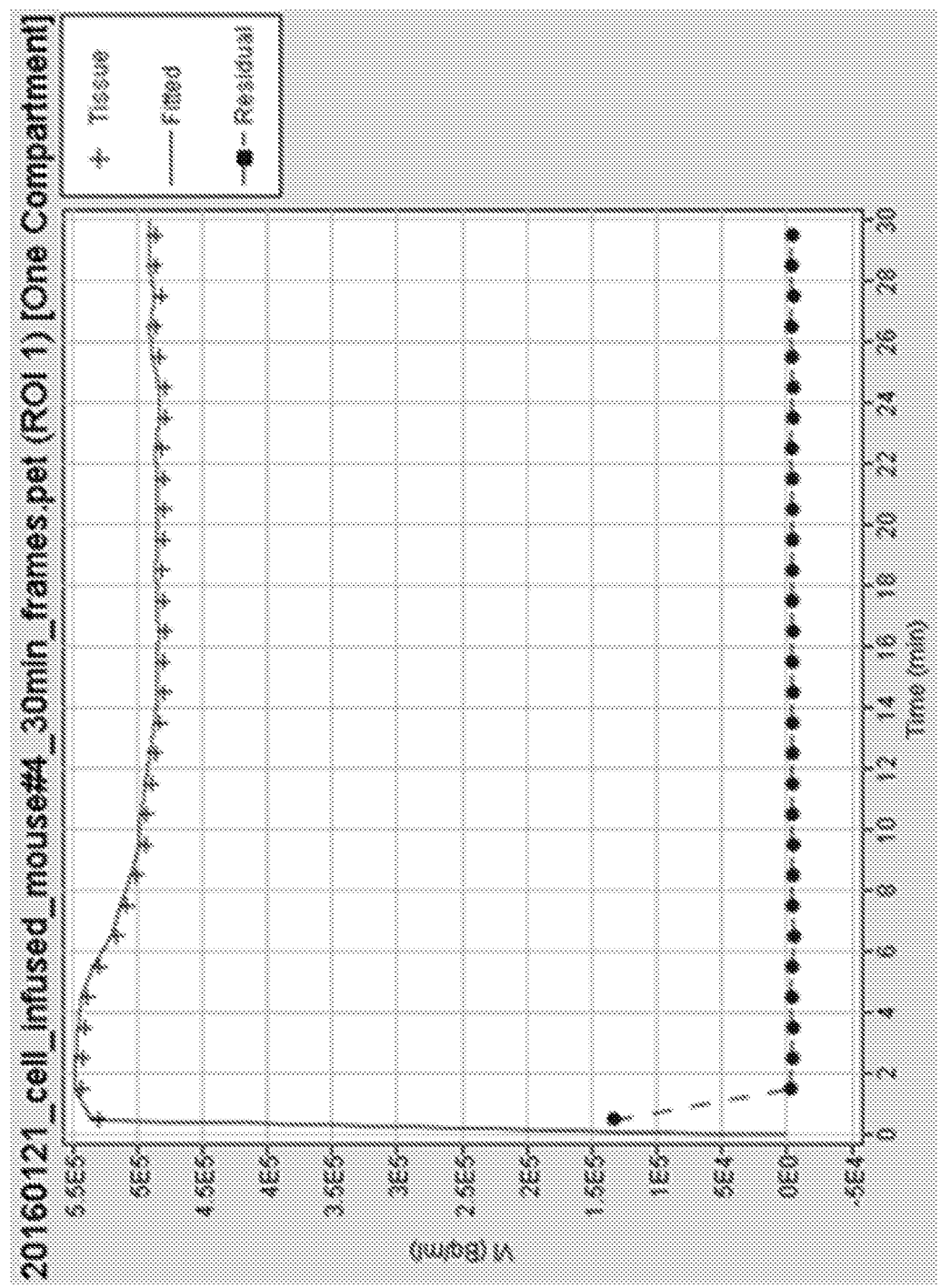

Fused microPET/CT images of the heart from these mice show clear differences in anatomic distribution of FDG in the heart. While marked myocardial uptake of FDG in the left ventricle of control mice is clearly visualized (FIG. 10), FDG distribution in the FDG-labeled RBC injected mice shows that the activity is essentially confined to the intraluminal chambers of the heart (FIG. 11). Pulmonary perfusion about the heart is also seen in these mice, unlike control mice.

Figure 16A:
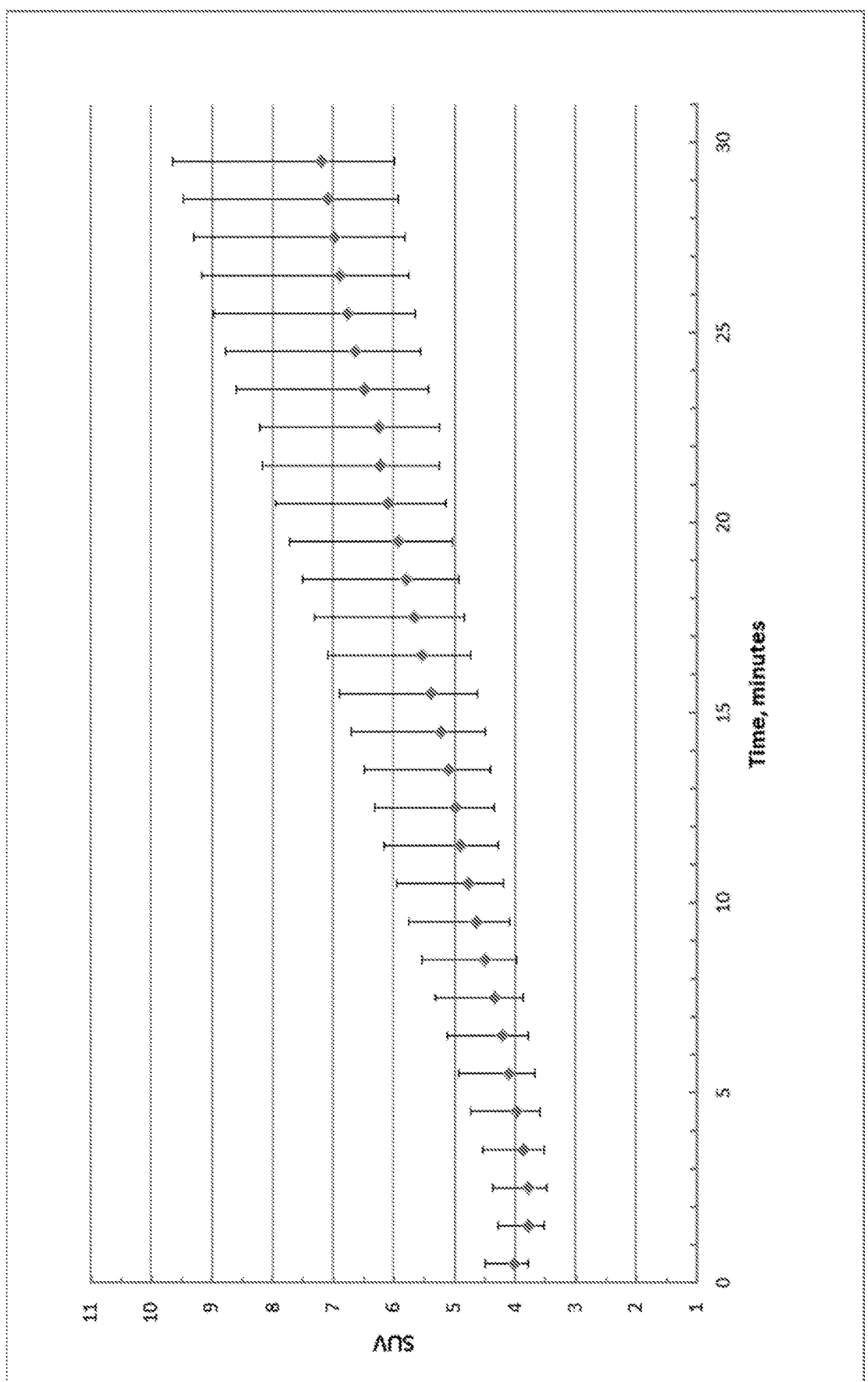
FIGS. 16A and 16B.
Figure 16B:
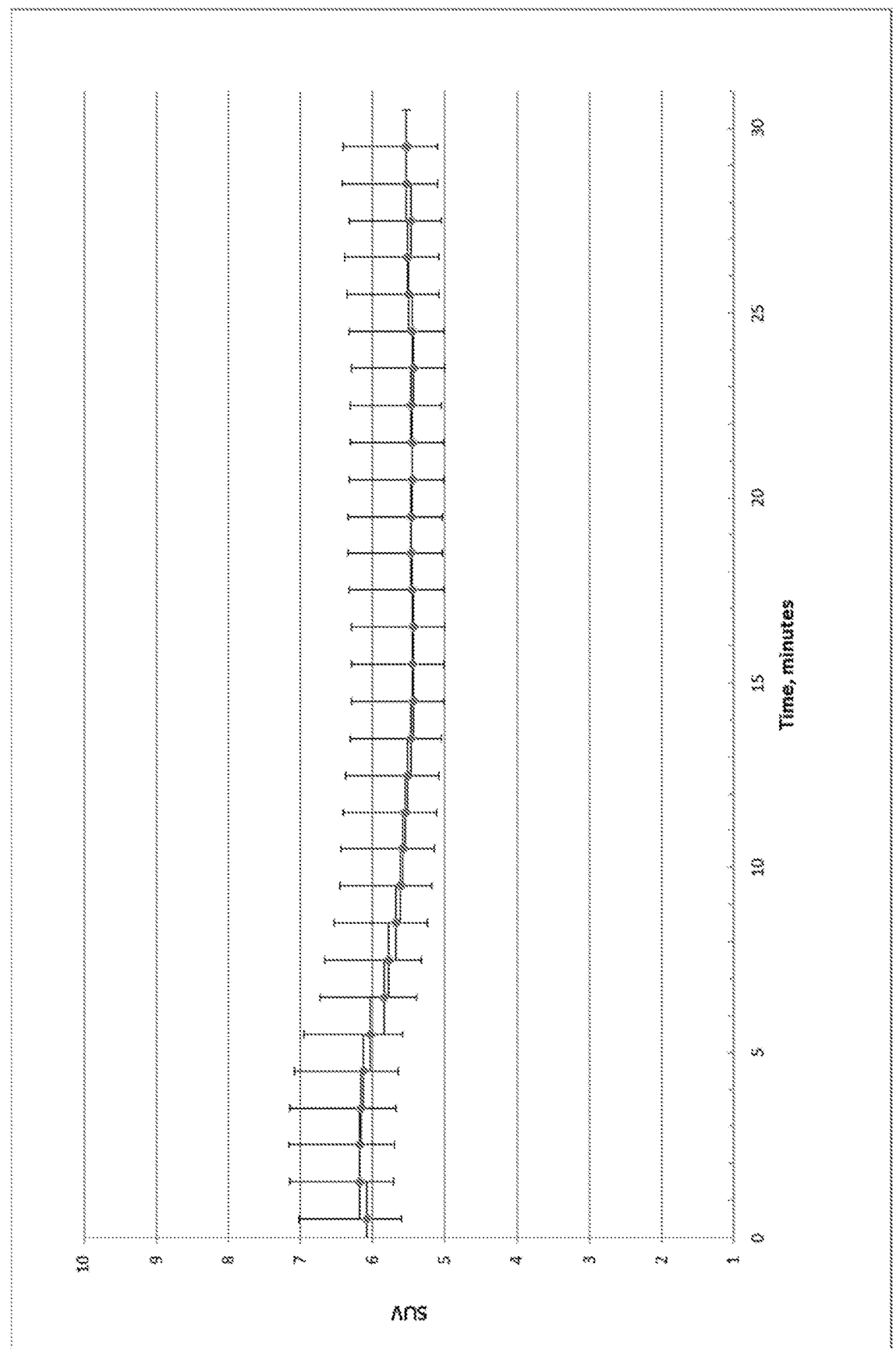

Time activity curves of the heart from these mice also show a pattern consistent with these differences in cardiac activity. FDG activity of the hearts of control mice increases steadily over the observation period of 20-30 minutes, consistent with progressive myocardial uptake of FDG (FIG. 16A). In FDG-labeled RBC injected mice, there is immediate high activity over the heart within 1 minute, followed by a small initial decline, then a plateau over most of the measured time period (FIG. 16B). FDG activity over the heart in these mice did not decline progressively over the observed time period to suggest significant in vivo RBC hemolysis and urinary excretion of released FDG in these mice.

Cardiac Cycle Rebinning of ECG-Gated Images of Heart in FDG-Labeled RBC Mice Allows for Visualization of Cardiac Contractility:

In addition, ECG-gated images from FDG-labeled RBC injected mice were rebinned according to the cardiac cycle to create cine images of cardiac motion in these mice.

Currently, $^{99m}$Tc-labeled compounds remain the dominant radionuclide-specific blood pool imaging agents used in the clinical setting worldwide. In particular, $^{99m}$Tc-labeled red blood cells are commonly used to non-invasively search for sites of occult lower intestinal bleeding and to measure cardiac contractility (ejection fraction) in patients at risk for chemotherapy-induced cardiotoxicity. Given the inherent advantages of PET over gamma camera imaging, development of 18-fluorine-based blood pool imaging agents for these and other clinical applications remains an area of active research.

We take advantage of the high physiologic glucose uptake rates of FDG by human erythrocytes to show that human erythrocytes can be internally labeled with an amount of FDG suitable for in vivo imaging of the vasculature of immunodeficient NSG mice with microPET/CT imaging. Rebinning of ECG-gated microPET images allowed for visualization of the cardiac cycle in the mouse heart.

While red blood cells collected ≤24 hours from the time of phlebotomy retained the ability to internalize significant amounts of FDG, we observed a negligible rate of internal FDG uptake when human RBCs are collected and used≈5 days after phlebotomy, suggesting a significant drop in FDG uptake by glucose transporters and/or intracellular FDG metabolism in these somewhat older cells.

FDG RBC labeling was accomplished using a straightforward incubation and wash procedure that can be completed in a relatively short period of time (≈60-70 minutes) and with minimal equipment. In addition, the simple incubation/wash buffer used in the protocol is composed of physiologic concentrations of a few natural salts, and a subclinical (≤1%) dose of the FDA approved chelating compound EDTA. These buffer constituents should thus not represent a real impediment to clinical use. (Lamas G A 2014) The results suggest that a single wash step would leave an acceptably small percentage of free FDG in the washed cell preparation, and is thus expected to be sufficiently suitable for clinical use. The inventor predicts that clinical translation of the above described FDG labeling/wash protocol should allow for up to 370 MBq of FDG incorporated in a volume of 10 ml's packed RBCs, starting from an initial 740 MBq FDG amount.

Given the lack of clinically significant adverse events associated with transfusion of either autologous red blood cells or intravenous FDG, it is hypothesized that intravenous administration of FDG-labeled autologous human red blood cells is unlikely to induce serious adverse clinical events. The inventor has shown that multiple centrifugation steps does result in a slow gradual accumulation of putative RBC membrane damage, as manifested by trypan blue exclusion staining; however, the inventor did not detect a significant amount of urinary FDG excretion via PET imaging in these mice to suggest vascular release of large amounts of intracellular FDG or byproducts from in vivo RBC hemolysis/membrane leakage. It is possible that the total number of centrifugation steps can be further reduced by combining wash steps with either the initial RBC isolation and/or at the end of FDG incubation, thus limiting the overall degree of RBC membrane damage. It is also likely that in the clinical setting, any mechanically damaged RBCs would largely be sequestered in the spleen, as this is the putative rationale for imaging patients with suspected/occult splenic tissue after injection of $^{99m}$Tc-labeled, heat-damaged autologous RBCs (MacDonald and Burrell, 2008).

Mice imaged with FDG-labeled human RBCs were previously splenectomized over theoretical concerns of xenogeneic-specific splenic sequestration of human RBCs. As such, delineating the degree of human RBC sequestration in the spleen of NSG mice specific to mechanical RBC membrane damage would be difficult to characterize. It is still possible that similar imaging results can be obtained in mice with intact spleens; however, this remains to be further investigated by our group. As adult mouse RBCs have been found to have minimal membrane expression of GLUT1 transporters, mouse blood pool imaging using FDG-labeled mouse RBCs was not attempted, as it was deemed not likely to be readily achievable (Montel-Hagen et al., 2008).

It was found that all mice infused with human RBCs survived after imaging; however, some of the mice subjected to repeat injections of human RBCs experienced tachycardia and respiratory distress during and immediately after imaging that resolved 24 hours later. The etiology behind these events is unclear, but could be related to transient pulmonary/systemic edema from the relatively rapid injection of a large volume (≈500 µl) of FDG-labeled RBCs, despite prior retro-orbital plexus phlebotomy. It could also be theoretically related to hematopoietic engraftment of residual peripheral blood mononuclear cells (PBMCs) contained in the first injection of human erythrocytes. Subsequent injection of human erythrocytes from a different human donor might have induced a type of allogeneic blood transfusion reaction in mice, although this remains somewhat speculative. This possibility could potentially be obviated in the future by using RBCs from a single human blood donor when repeated mouse blood pool imaging is to be performed.

Conclusion:

It is shown herein that human erythrocytes can physiologically incorporate significant amounts of FDG in a timely manner which can then be used to obtain in vivo images of the vasculature using microPET/CT. As modern clinical PET/CT scanners generally possess count detection sensitivities significantly higher than that of clinical gamma scintigraphic cameras, FDG-RBC PET imaging may achieve comparable results to $^{99m}$Tc-labeled RBC imaging while allowing for a potentially significant overall reduction in patient radiation dose. Quantitative organ dosimetry modeling is required for further clarification of these issues, and is currently being pursued by our group.

Given the relative advantages of using FDG as a PET blood pool tracer, as well as the effectiveness and practicality of the red blood cell labeling procedure, this imaging technique can be of value for both laboratory investigators seeking to characterize altered blood volume/vasculature in animal models and veterinary patients of various pathologies, as well as for nuclear medicine physicians interested in other translational blood pool and blood perfusion imaging applications for human patients.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Exemplified embodiments of the invention include, but are not limited to:

Embodiment 1

A method for in vivo imaging of red blood cells (RBCs) using positron emission tomography (PET), comprising:
  introducing red blood cells (RBCs) internally labeled with 2-deoxy-2-($^{18}$F)fluoro-D-glucose (FDG) (FDG-RBCs) into the circulatory system of a human or non-human animal subject in vivo; and
  PET imaging the introduced FDG-RBCs in the subject.

Embodiment 2

The method of embodiment 1, wherein introducing comprises introducing the FDG-RBCs intravascularly (e.g., by intravenous or intra-arterial injection or infusion).

Embodiment 3

The method of embodiment 1 or 2, further comprising, prior to introducing:
  withdrawing RBCs from the subject; and
  labeling the withdrawn RBCs with FDG to produce the FDG-RBCs.

Embodiment 4

The method of embodiment 2 or 3, wherein prior to said introducing, labeling of the RBCs comprises incubating the RBCs with FDG, and wherein the method further comprises purifying the FDG-RBCs from incorporated (free) FDG prior to said introducing.

Embodiment 5

The method of embodiment 4, wherein said purifying comprises centrifugation and cell washing.

Embodiment 6

The method of any one of embodiments 1 to 5, wherein said imaging comprises imaging a blood perfusion-dependent phenomena.

Embodiment 7

The method of embodiment 6, wherein said imaging comprises myocardial perfusion imaging (MPI) or cardiac contractility.

Embodiment 8

The method of embodiment 6, wherein the blood perfusion-dependent phenomena is tissue ischemia or tissue perfusion.

Embodiment 9

The method of embodiment 8, wherein the subject has suffered a stroke or undergone organ transplantation or tissue grafting.

Embodiment 10

The method of embodiment 6, wherein the blood perfusion-dependent phenomena is internal bleeding or tumor perfusion.

Embodiment 11

The method of any one of embodiments 1 to 6, wherein said imaging comprises imaging one or more sites of internal bleeding in the subject.

Embodiment 12

The method of any one of 1 to 5, wherein the imaging is used for dynamic cardiac contractility assessment, or localization of sites of occult gastrointestinal (GI) bleeding.

Embodiment 13

The method of any one of embodiments 1 to 12, wherein said imaging comprises combined positron emission tomography-computed tomography ("PET-CT") imaging.

Embodiment 14

The method of any one of embodiments 1 to 13, wherein the subject is a human.

Embodiment 15

The method of any one of embodiments 1 to 13, wherein the subject is a non-human animal.

Embodiment 16

A method of preparing red blood cells (RBCs) of a human or non-human animal for positron emission tomography (PET), comprising labeling RBCs in vitro with 2-deoxy-2-($^{18}$F)fluoro-D-glucose (FDG) to produce FDG-labeled RBCs.

Embodiment 17

A positron emission tomography (PET) contrast agent comprising an RBC internally labeled with 2-deoxy-2-($^{18}$F)fluoro-D-glucose (FDG).

REFERENCES

Bailey D L, Eslick E M, Schembri G P, Roach P J. (68)Ga PET Ventilation and Perfusion Lung Imaging-Current Status and Future Challenges. *Seminars In Nuclear Medicine*. September 2016; 46(5):428-435.

Basuli F, Li C, Xu B, et al. Synthesis of fluorine-18 radio-labeled serum albumins for PET blood pool imaging. *Nuclear medicine and biology*. March 2015; 42(3): 219-225.

Bonte F J, Hynan L, Harris T S, White C L, 3rd. TC-99m HMPAO Brain Blood Flow Imaging in the Dementias with Histopathologic Correlation in 73 Patients. *International Journal Of Molecular Imaging.* 2011; 2011: 409101.

Burow R D, Strauss H W, Singleton R, et al. Analysis of left ventricular function from multiple gated acquisition cardiac blood pool imaging. Comparison to contrast angiography. *Circulation.* December 1977; 56(6):1024-1028.

Cox. B. et al. The Sweet Spot: FDG and other 2-carbon glucose analogs for multi-modal metabolic imaging of tumor metabolism. *American Journal of Nuclear Medicine and Molecular Imaging.* 2015; Vol 5, No. 1, pp. 1-13.

de Langen A J, van den Boogaart V E, Marcus J T, Lubberink M. Use of H2(15)O-PET and DCE-MRI to measure tumor blood flow. *The Oncologist.* June 2008; 13(6):631-644.

Fahey, F H. "Data Acquisition in PET Imaging" *J. Nucl Med Technol,* 2002, 30:39-49.

Fan A P, Jahanian H, Holdsworth S J, Zaharchuk G. Comparison of cerebral blood flow measurement with [150]-water positron emission tomography and arterial spin labeling magnetic resonance imaging: A systematic review. *Journal Of Cerebral Blood Flow And Metabolism.* May 2016; 36(5):842-861.

Flower Mass., Zweit J, Hall A D, et al. 62Cu-PTSM and PET used for the assessment of angiotensin II-induced blood flow changes in patients with colorectal liver metastases. *European Journal Of Nuclear Medicine.* January 2001; 28(1):99-103.

Goffin K, Dedeurwaerdere S, Van Laere K, Van Paesschen W. Neuronuclear assessment of patients with epilepsy. *Seminars In Nuclear Medicine.* July 2008; 38(4):227-239.

Green Mass., Klippenstein D L, Tennison J R. Copper(II) bis(thiosemicarbazone) complexes as potential tracers for evaluation of cerebral and myocardial blood flow with PET. *Journal Of Nuclear Medicine.* September 1988; 29(9):1549-1557.

Green Mass., Mathias C J, Welch M J, et al. Copper-62-labeled pyruvaldehyde bis(N4-methylthiosemicarbazonato)copper(II): synthesis and evaluation as a positron emission tomography tracer for cerebral and myocardial perfusion. *Journal Of Nuclear Medicine.* December 1990; 31(12):1989-1996.

Hajjawi O. Glucose transport in human red blood cells. *American Journal of Biomedical and Life Sciences.* 2013; Vol 1, No. 3., pp. 44-52.

Haynes N G, Lacy J L, Nayak N, et al. Performance of a 62Zn/62Cu generator in clinical trials of PET perfusion agent 62Cu-PTSM. *Journal Of Nuclear Medicine.* February 2000; 41(2):309-314.

Herrero P, Hartman J J, Green Mass., et al. Regional myocardial perfusion assessed with generator-produced copper-62-PTSM and PET. *Journal Of Nuclear Medicine.* August 1996; 37(8):1294-1300.

Ibaraki M, Miura S, Shimosegawa E, et al. Quantification of cerebral blood flow and oxygen metabolism with 3-dimensional PET and 150: validation by comparison with 2-dimensional PET. *Journal of Nuclear Medicine.* January 2008; 49(1):50-59.

Lin L. "A Concordance Correlation of Coefficient to Evaluate Reproducibility" *Biometrics,* 1989, 45(1):255-268.

Lodge Mass., Jacene H A, Pili R, Wahl R L. Reproducibility of tumor blood flow quantification with 150-water PET. *Journal Of Nuclear Medicine.* October 2008; 49(10): 1620-1627.

MacDonald A, Burrell S. Infrequently performed studies in nuclear medicine: Part 1. *Journal of nuclear medicine technology.* September 2008; 36(3):132-143; quiz 145.

Montel-Hagen A, et al. The Glut1 and Glut4 glucose transporters are differentially expressed during perinatal and postnatal erythropoiesis. *Blood.* Dec. 1, 2008. Vol 112, No. 12, pp. 4729-4738.

Montel-Hagen, A. et al. "Erythrocyte Glut1 triggers DHA uptake in mammals unable to synthesize Vitamin C" *Cell,* Mar. 21, 2008, 132:1039-1048.

Niu G, Lang L, Kiesewetter D O, et al. In Vivo Labeling of Serum Albumin for PET. *Journal Of Nuclear Medicine.* July 2014; 55(7): 1150-1156.

Patlak C S, Blasberg R G, Fenstermacher J D. Graphical evaluation of blood-to-brain transfer constants from multiple-time uptake data. *Journal Of Cerebral Blood Flow And Metabolism.* March 1983; 3(1): 1-7.

Rahmin A, Zaidi H. PET versus SPECT: strengths, limitations and challenges. *Nuclear Medicine Communications.* 2008. Vol. 29, pp. 193-207.

Saatchi K, Gelder N, Gershkovich P, et al. Long-circulating non-toxic blood pool imaging agent based on hyperbranched polyglycerols. *International Journal of Pharmaceutics.* Jan. 17, 2012; 422(1-2):418-427.

Saha, G B. Basics of PET Imaging: Physics, Chemistry, and Regulations—Chapter 6: "Performance Characteristics of PET Scanners" Springer Science, 2010, pp. 97-116.

Shelton Me., Green Mass., Mathias C J, Welch M J, Bergmann S R. Assessment of regional myocardial and renal blood flow with copper-PTSM and positron emission tomography. *Circulation.* September 1990; 82(3):990-997.

Tahara N. et al. 2-deoxy-2-[$^{18}$F]Fluoro-D-Mannose Positron Emission Tomography Imaging in Atherosclerosis. *Nature Medicine.* 2014; Vol 20, No. 2, pp. 215-221.

Thorne D A, Datz F L, Remley K, Christian P E. Bleeding rates necessary for detecting acute gastrointestinal bleeding with technetium-99m-labeled red blood cells in an experimental model. *Journal Of Nuclear Medicine.* April 1987; 28(4):514-520.

Viskupicova J, Blaskovic D, Galiniak S, et al. Effect of high glucose concentrations on human erythrocytes in vitro. *Redox Biology.* August 2015; 5:381-387.

Wallhaus T R, Lacy J, Stewart R, et al. Copper-62-pyruvaldehyde bis(N-methylthiosemicarbazone) PET imaging in the detection of coronary artery disease in humans. *Journal Of Nuclear Cardiology.* January-February 2001; 8(1):67-74.

Wang Z G, Zhang G X, Hao S H, et al. Technological value of SPECT/CT fusion imaging for the diagnosis of lower gastrointestinal bleeding. *Genetics And Molecular Research.* Nov. 24, 2015; 14(4):14947-14955.

Welch M J, McCarthy T J. The potential role of generator-produced radiopharmaceuticals in clinical PET. *Journal Of Nuclear Medicine.* February 2000; 41(2):315-317.

Wong T Z, Lacy J L, Petry N A, et al. PET of hypoxia and perfusion with 62Cu-ATSM and 62Cu-PTSM using a 62Zn/62Cu generator. *American Journal Of Roentgenology.* February 2008; 190(2):427-432.

Zhang T, Das S K, Fels D R, et al. PET with 62Cu-ATSM and 62Cu-PTSM is a useful imaging tool for hypoxia and perfusion in pulmonary lesions. *American Journal Of Roentgenology.* November 2013; 201(5):W698-706.

I claim:

1. A method for in vivo imaging of red blood cells (RBCs) in a human or non-human animal subject using positron emission tomography (PET), comprising:
   withdrawing RBCs from the subject;
   internally labeling the withdrawn RBCs with 2-deoxy-2-($^{18}$F)fluoro-D-glucose (FDG) to produce the RBCs internally labeled with FDG (FDG-RBCs), wherein said internally labeling comprises incubating the withdrawn RBCs with FDG;

purifying the FDG-RBCs from unincorporated FDG;

introducing the purified FDG-RBCs into the circulatory system of the subject in vivo; and PET imaging the introduced FDG-RBCs in the subject.

2. The method of claim 1, wherein said introducing comprises introducing the FDG-RBCs by intravenous or intra-arterial injection or infusion.

3. The method of claim 1, wherein said imaging comprises imaging a blood perfusion-dependent phenomenon.

4. The method of claim 3, wherein said imaging comprises myocardial perfusion imaging (MPI) or cardiac contractility.

5. The method of claim 3, wherein the blood perfusion-dependent phenomena is tissue ischemia or tissue perfusion.

6. The method of claim 5, wherein the subject has suffered a stroke or undergone organ transplantation or tissue grafting.

7. The method of claim 3, wherein the blood perfusion-dependent phenomena is internal bleeding or tumor perfusion.

8. The method of claim 1, wherein said imaging comprises imaging one or more sites of internal bleeding in the subject.

9. The method of claim 1, wherein said imaging is of an anatomical region useful for dynamic cardiac contractility assessment.

10. The method of claim 1, wherein said imaging is of an anatomical region useful for localization of sites of occult gastrointestinal (GI) bleeding.

11. The method of claim 1, wherein said imaging is cerebral vascular imaging.

12. The method of claim 11, wherein the subject has, is suspected of having, or is at risk of having, Alzheimer's disease or other neurodegenerative disease.

13. The method of claim 1, wherein said imaging comprises combined positron emission tomography-computed tomography ("PET-CT") imaging.

14. The method of claim 1, wherein the subject is a human.

15. A kit comprising:

2-deoxy-2-($^{18}$F)fluoro-D-glucose (FDG), sodium chloride, potassium chloride, and at least one of ethylenediaminetetraacetic acid (EDTA), heparin, and sodium citrate.

16. The method of claim 1, wherein said internally labeling the withdrawn RBCs with FDG to produce the FDG-RBCs comprises incubating the withdrawn RBCs with 1-2 mCi $^{18}$F-FDG at 37° C. for 30 minutes.

17. The method of claim 1, wherein said purifying the FDG-RBCs from unincorporated FDG comprises centrifuging the FDG-RBCs for 10 minutes at 1000×g and removing the supernatant containing unincorporated FDG.

18. The method of claim 17, further comprising washing the centrifuged FDG-RBCs with an EDTA buffer and centrifuging the washed FDG-RBCs.

19. A method for in vivo imaging of red blood cells (RBCs) in a human or non-human animal subject using positron emission tomography (PET), comprising:

withdrawing RBCs from the subject;

internally labeling the withdrawn RBCs with 2-deoxy-2-($^{18}$F)fluoro-D-glucose (FDG) to produce the RBCs internally labeled with FDG (FDG-RBCs), wherein said internally labeling comprises incubating the withdrawn RBCs with 1-2 mCi $^{18}$F-FDG at 37° C. for 30 minutes;

purifying the FDG-RBCs from unincorporated FDG by centrifuging the FDG-RBCs for 10 minutes at 1000×g and removing the supernatant containing unincorporated FDG;

introducing the purified FDG-RBCs into the circulatory system of the subject in vivo; and PET imaging the FDG-RBCs introduced into the subject.

20. The method of claim 19, wherein the subject is a human.

* * * * *

UNITED STATES PATENT AND TRADEMARK OFFICE
CERTIFICATE OF CORRECTION

PATENT NO. : 10,561,379 B2
APPLICATION NO. : 15/780568
DATED : February 18, 2020
INVENTOR(S) : Jung Wook Choi Page 1 of 1

It is certified that error appears in the above-identified patent and that said Letters Patent is hereby corrected as shown below:

In the Specification

Column 17,
Line 51, "to 370" should read --to $\approx$ 370--.

Signed and Sealed this
Twenty-third Day of June, 2020

Andrei Iancu
*Director of the United States Patent and Trademark Office*